US008835481B2

(12) United States Patent
Guglielmotti et al.

(10) Patent No.: US 8,835,481 B2
(45) Date of Patent: Sep. 16, 2014

(54) 1-BENZYL-3-HYDROXYMETHYLINDAZOLE DERIVATIVES AND USE THEREOF IN THE TREATMENT OF DISEASES BASED ON THE EXPRESSION OF MCP-1, CX3CR1 AND P40

(75) Inventors: Angelo Guglielmotti, Rome (IT); Guido Furlotti, Rome (IT); Giorgina Mangano, Rome (IT); Nicola Cazzolla, Albano Laziale (IT); Barbara Garofalo, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 78 days.

(21) Appl. No.: 12/865,923

(22) PCT Filed: Mar. 5, 2009

(86) PCT No.: PCT/EP2009/052585
§ 371 (c)(1),
(2), (4) Date: Aug. 3, 2010

(87) PCT Pub. No.: WO2009/109613
PCT Pub. Date: Sep. 11, 2009

(65) Prior Publication Data
US 2011/0003874 A1     Jan. 6, 2011

(30) Foreign Application Priority Data

Mar. 7, 2008 (EP) ..................................... 08425139

(51) Int. Cl.
*A61K 31/416* (2006.01)
*C07D 231/56* (2006.01)

(52) U.S. Cl.
CPC ................................... *C07D 231/56* (2013.01)
USPC ........................................ 514/406; 548/362.5

(58) Field of Classification Search
None
See application file for complete search history.

(56) References Cited

U.S. PATENT DOCUMENTS 4,999,367 A * 3/1991 Baiocchi et al. ............... 514/403

FOREIGN PATENT DOCUMENTS

| EP | 0 382 276 B1 | 8/1995 |
|---|---|---|
| EP | 0 510 748 B1 | 3/1996 |
| EP | 1 185 528 | 3/2002 |
| EP | 1 188 438 A1 | 3/2002 |
| EP | 1 199 074 A1 | 4/2002 |
| EP | 1 005 332 B1 | 10/2003 |
| EP | 1 369 119 A1 | 12/2003 |
| EP | 1 458 687 | 9/2004 |
| EP | 1 675 862 | 7/2006 |
| EP | 1 819 341 | 8/2007 |
| EP | 1 827 447 | 9/2007 |
| EP | 1 869 055 | 12/2007 |
| EP | 1 869 056 | 12/2007 |
| WO | WO 99/04770 A2 | 2/1999 |
| WO | WO 99/04770 A3 | 2/1999 |
| WO | WO 00/78757 A1 | 12/2000 |
| WO | WO 03/047516 A2 | 6/2003 |
| WO | WO 2005/033115 A1 | 4/2005 |
| WO | WO 2006/053227 A2 | 5/2006 |
| WO | WO 2006/060194 A1 | 6/2006 |
| WO | WO 2006/107257 A1 | 10/2006 |
| WO | WO 2006/107258 A1 | 10/2006 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Barrett J. Rollins, "Chemokines", Blood, vol. 90, No. 3, Aug. 1, 1997, 23 Pages.
Marco Baggiolini, "Chemokines and Leukocyte Traffic", Nature, vol. 392, Apr. 9, 1998, pp. 565-568.
Craig Gerard et al., "Chemokines and Disease", Nature Immunology, vol. 2, No. 2, Feb. 2001, pp. 108-115.
Surendran Mahalingam et al., "Chemokines and Viruses: Friends or Foes?", Trends in Microbiology, vol. 11, No. 8, Aug. 2003, pp. 383-391.
Nestor E. Rulli et al., "Ross River Virus: molecular and Cellular Aspects of Disease Pathogenesis", Pharmacology and Therapeutics, vol. 107, 2005, pp. 329-342.
Toshihiro Nanki et al., "Migration of CX3CR1-Positive T Cells Producing Type 1 Cytokines and Cytotoxic Molecules into the Synovium of Patients with Rheumatoid Arthritis", Arthritis and Rheumatism, vol. 46, No. 11, Nov. 2002, pp. 2878-2883.
Stephan Segerer et al., "Expression of the Fractalkine Receptor (CX3CR1) in Human Kidney Diseases", Kidney International, vol. 62, 2002, pp. 488-495.
Miquel Sans et al., "Enhanced Recruitment of CX3CR1+ T Cells by Mucosal Endothelial Cell-Derived Fractalikine in Inflammatory Bowel Disease", Gastroenterology, vol. 132, No. 1, 2007, pp. 139-153.

(Continued)

*Primary Examiner* — Samantha Shterengarts
(74) *Attorney, Agent, or Firm* — Oblon, Spivak, McClelland, Maier & Neustadt, L.L.P.

(57) ABSTRACT

The present invention relates to novel 1-benzyl-3-hydroxymethylindazole derivatives according to Formula (I) described in the claims, and to a pharmaceutical composition comprising them, together with a pharmaceutically acceptable vehicle. In addition, the present invention relates to the use of 1-benzyl-3-hydroxymethylindazole derivatives for the preparation of a pharmaceutical composition that is active in the treatment of diseases based on the expression of MCP-1, CX3CR1 and p40, and to their use in a method for treating or preventing diseases based on the expression of MCP-1, CX3CR1 and p40.

22 Claims, No Drawings

(56) References Cited

OTHER PUBLICATIONS

Ping Liu et al., "Cross Talk Among Smad, MAPK, and Integrin Signaling Pathways Enhances Adventitial Fibroblast Functions Activated by Transforming Growth Factor $^21$ and Inhibited by Gax", Arteriosclerosis, Thrombosis, and Vascular Biology, vol. 28, Jan. 10, 2008, 23 Pages.

David H. McDermott et al., "Chemokine Receptor Mutant CX3CR1-M280 has Impaired Adhesive Function and Correlates with Protection from Cardiovascular Disease in Humans", The Journal of Clinical Investigation, vol. 111, No. 8, Apr. 2003, pp. 1241-1250.

Alexander Niessner et al., "Wound Healing and Inflammation/Infection: Fractalkine Receptor Polymorphisms V249I and T280M as Genetic Risk Factors for Restenosis", Thrombosis and Haemostasis, vol. 94, 2005, pp. 1251-1256.

Dr. John Koo, "Population-Based Epidemiologic Study of Psoriasis with Emphasis on Quality of Life Assessment", Psychodermatology, vol. 14, No. 3, Jul. 1996, pp. 485-496.

Dr. Michael P. Schoen et al., "Medical Progress: Psoriasis", The New England Journal of Medicine, vol. 352, No. 18, May 5, 2005, pp. 1899-1912.

Marina Sironi et al., "A Small Synthetic Molecule Capable of Preferentially Inhibiting the Production of the CC Chemokine Monocyte Chemotactic Protein-1", European Cytokine Network, vol. 10, No. 3, Sep. 1999, pp. 437-441.

U.S. Appl. No. 12/864,767, filed Jul. 27, 2010, Guglielmotti, et al.
U.S. Appl. No. 12/865,792, filed Aug. 2, 2010, Guglielmotti, et al.
U.S. Appl. No. 12/866,814, filed Aug. 9, 2010, Guglielmotti, et al.
U.S. Appl. No. 13/497,175, filed May 2, 2012, Guglielmotti, et al.
U.S. Appl. No. 13/898,950, filed May 21, 2013, Guglielmotti, et al.
U.S. Appl. No. 13/618,948, filed Sep. 14, 2012, Guglielmotti, et al.
U.S. Appl. No. 13/041,557, filed Mar. 7, 2011, Guglielmotti, et al.

Office Action as received in the corresponding European Patent Application No. 09 717 638.2-1462 dated Jun. 27, 2014.

S. Gazzaniga, et al., "Targeting Tumor-Associated Macrophages and Inhibition of MCP-1 Reduce Angiogenesis and Tumor Growth in a Human Melanoma Xenograft", The Society for Investigative Dermatology, vol. 127, No. 8, Apr. 26, 2007, pp. 2031-2041.

C. Zoja, et al., "Bindarit retards renal disease and prolongs survival in murine lupus autoimmune disease", Kidney International, Mar. 1, 1998, pp. 726-734C Zoia, et al., "Bindarit retards renal disease and prolongs survival in murine lupus autoimmune disease", Kidney International, Mar. 1, 1998, pp. 726-734.

A. Guglielmotti, et al., "Amelioration of rat adjuvant arthritis by therapeutic treatment with bindarit, an inhibitor of MCP-1 and TNF-[alpha] production", Inflammation Research, vol. 51, No. 5, May 1, 2002, pp. 252-258.

* cited by examiner

1-BENZYL-3-HYDROXYMETHYLINDAZOLE DERIVATIVES AND USE THEREOF IN THE TREATMENT OF DISEASES BASED ON THE EXPRESSION OF MCP-1, CX3CR1 AND P40

CROSS-REFERENCE TO RELATED APPLICATIONS

This application is a 371 of PCT/EP09/52585 filed Mar. 5, 2009 and claims the benefit of EP 08425139.6 filed Mar. 7, 2008.

FIELD OF THE INVENTION

The present invention relates to 1-benzyl-3-hydroxymethylindazole derivatives, to a pharmaceutical composition comprising them, and to their use in the treatment of diseases based on the expression of MCP-1, CX3CR1 and p40.

In particular, the present invention relates to novel 1-benzyl-3-hydroxymethylindazole derivatives according to formula (I) below, and to a pharmaceutical composition comprising them together with a pharmaceutically acceptable vehicle. In addition, the present invention relates to the use of 1-benzyl-3-hydroxymethylindazole derivatives for preparing a pharmaceutical composition that is active in the treatment of diseases based on the expression of MCP-1, CX3CR1 and p40, and to their use in a method for treating or preventing diseases based on the expression of MCP-1, CX3CR1 and p40.

BACKGROUND OF THE ART

As is known, MCP-1 (Monocyte Chemotactic Protein-1) is a protein belonging to the β subfamily of chemokines. MCP-1 has powerful chemotactic action on monocytes and exerts its action also on T lymphocytes, mastocytes and basophils (Rollins B. J., Chemokines, Blood 1997; 90: 909-928; M. Baggiolini, Chemokines and leukocyte traffic, Nature 1998; 392: 565-568).

Other chemokines belonging to the β subfamily are, for example, MCP-2 (Monocyte Chemotactic Protein-2), MCP-3, MCP-4, MIP-1α and MIP-1β, RANTES.

The β subfamily differs from the α subfamily in that, in the structure, the first two cysteines are adjacent for the β subfamily, whereas they are separated by an intervening amino acid for the α subfamily.

MCP-1 is produced by various types of cells (leukocytes, platelets, fibroblasts, endothelial cells and smooth muscle cells).

Among all the known chemokines, MCP-1 shows the highest specificity for monocytes and macrophages, for which it constitutes not only a chemotactic factor but also an activation stimulus, consequently inducing processes for producing numerous inflammatory factors (superoxides, arachidonic acid and derivatives, cytokines/chemokines) and amplifying the phagocytic activity.

The secretion of chemokines in general, and of MCP-1 in particular, is typically induced by various pro-inflammatory factors, for instance interleukin-1 (IL-1), interleukin-2 (IL-2), TNFα (Tumour Necrosis Factor α), interferon-γ and bacterial lipopolysaccharide (LPS).

Prevention of the inflammatory response by blocking the chemokine/chemokine receptor system represents one of the main targets of pharmacological intervention (Gerard C. and Rollins B. J., Chemokines and disease. Nature Immunol. 2001; 2:108-115).

There is much evidence to suggest that MCP-1 plays a key role during inflammatory processes and has been indicated as a new and validated target in various pathologies.

Evidence of a considerable physiopathological contribution of MCP-1 has been obtained in the case of patients with articular and renal inflammatory diseases (rheumatoid arthritis, lupus nephritis, diabetic nephropathy and rejection following transplant).

However, more recently, MCP-1 has been indicated among the factors involved in inflammatory pathologies of the CNS (multiple sclerosis, Alzheimer's disease, HIV-associated dementia) and other pathologies and conditions, with and without an obvious inflammatory component, including atopic dermatitis, colitis, interstitial lung pathologies, restenosis, atherosclerosis, complications following a surgical intervention (for instance angioplasty, arterectomy, transplant, organ and/or tissue replacement, prosthesis implant), cancer (adenomas, carcinomas and metastases) and even metabolic diseases such as insulin resistance and obesity.

In addition, despite the fact that the chemokine system is involved in controlling and overcoming viral infections, recent studies have demonstrated that the response of certain chemokines, and in particular of MCP-1, may have a harmful role in the case of host-pathogen interactions. In particular, MCP-1 has been indicated among the chemokines that contribute towards organ and tissue damage in pathologies mediated by alpha viruses characterized by monocyte/macrophage infiltration in the joints and muscles (Mahalingam S. et al. Chemokines and viruses: friend or foes? Trends in Microbiology 2003; 11: 383-391; Rulli N. et al. Ross River Virus: molecular and cellular aspects of disease pathogenesis. 2005; 107: 329-342).

Monocytes are the main precursors of macrophages and dendritic cells, and play a critical role as mediators of inflammatory processes. CX3CR1, with its ligand CX3CL1 (fractalkine), represents a key factor in regulating the migration and adhesiveness of monocytes. CX3CR1 is expressed in monocytes, whereas CX3CL1 is a transmembrane chemokine in endothelial cells. Genetic studies in man and in animal models have demonstrated an important role in the physiopathology of inflammatory diseases of CX3CR1 and CX3CL1. There is in fact much evidence to suggest a key contribution of CX3CR1 and of its ligand in the pathogenesis and progression of articular, renal, gastrointestinal and vascular inflammatory diseases (e.g. rheumatoid arthritis, lupus nephritis, diabetic nephropathy, Crohn's disease, ulcerative colitis, restenosis and atherosclerosis).

The expression of CX3CR1 is over-regulated in T cells, which are believed to accumulate in the synovium of patients suffering from rheumatoid arthritis. In addition, the expression of CX3CL1 is over-regulated in endothelial cells and fibroblasts present in the synovium of these patients. Consequently, the CX3CR1/CX3CL1 system plays an important role in controlling the type of cell and the mode of infiltration of the synovium and contributes towards the pathogenesis of rheumatoid arthritis (Nanki T. et al., "Migration of CX3CR1-positive T cells producing type 1 cytokines and cytotoxic molecules into the synovium of patients with rheumatoid arthritis", Arthritis & Rheumatism (2002), vol. 46, No. 11, pp. 2878-2883).

In patients suffering form renal damage, the majority of the inflammatory leukocytes that infiltrate the kidneys express CX3CR1, and in particular it is expressed on two of the main cell types involved in the most common inflammatory renal pathologies and in kidney transplant rejection, T cells and monocytes (Segerer S. et al., Expression of the fractalkine receptor (CX3CR1) in human kidney diseases, Kidney International (2002) 62, pp. 488-495).

Participation of the CX3CR1/CX3CL1 system has been suggested also in inflammatory bowel diseases (IBD). In point of fact, in the case of patients suffering from IBD (e.g. Crohn's disease, ulcerative colitis), a significant increase in the production of CX3CL1 by the intestinal capillary system and a significant increase in CX3CR1-positive cells have been demonstrated, both at the circulatory level and in the mucosa (Sans M. et al., "Enhanced recruitment of CX3CR1+T cells by mucosal endothelial cell-derived fractalkine in inflammatory bowel diseases", Gastroenterology 2007, vol. 132, No. 1, pp. 139-153).

Even more interesting is the demonstration of the key role played by the CX3CR1/CX3CL1 system in vascular damage and in particular under pathological conditions, for instance atherosclerosis and restenosis. CX3CR1 is indicated as a critical factor in the process of infiltration and accumulation of monocytes in the vascular wall, and CX3CR1 polymorphism in man is associated with a reduced prevalence of atherosclerosis, coronary disorders and restenosis (Liu P. et al., "Cross-talk among Smad, MAPK and integrin signalling pathways enhances adventitial fibroblast functions activated by transforming growth factor-1 and inhibited by Gax" Arterioscler. Thromb. Vasc. Biol. 2008; McDermott D. H. et al., "Chemokine receptor mutant CX3CR1-M280 has impaired adhesive function and correlates with protection from cardiovascular diseases in humans", J. Clin. Invest. 2003; Niessner A. et al., Thrombosis and Haemostasis 2005).

IL-12 and IL-23 are members of a small family of proinflammatory heterodimeric cytokines. Both cytokines share a common subunit, p40, which is covalently bonded either to the p35 subunit to produce the mature form of IL-12, or to the p19 subunit to produce the mature form of IL-23. The receptor for IL-12 is constituted by the subunits IL-12R$\beta$1 and IL-12R$\beta$2, while the receptor for IL-23 is constituted by the subunits IL-12R$\beta$1 and IL-23R.

IL-12 and IL-23 are mainly expressed by activated dendritic cells and by phagocytes. The receptors for the two cytokines are expressed on the T and NK cells, and NK T cells, but low levels of complexes of the receptor for IL-23 are also present in monocytes, macrophages and dendritic cells.

Despite these similarities, there is much evidence to suggest that IL-12 and IL-23 control different immunological circuits. In point of fact, whereas IL-12 controls the development of Th1 cells, which are capable of producing gamma-interferon (IFN-$\gamma$), and increases the cytotoxic, antimicrobial and antitumoral response, IL-23 regulates a circuit that leads to the generation of CD4$^+$ cells, which are capable of producing IL-17. The induction of IL-23-dependent processes leads to the mobilization of various types of inflammatory cell, for instance $T_H$-17, and it has been demonstrated as being crucial for the pathogenesis of numerous inflammatory pathologies mediated by immonological responses.

Typical examples of pathologies associated with the expression of p40 are chronic inflammatory diseases of the articular apparatus (e.g. rheumatoid arthritis), of the dermatological apparatus (e.g. psoriasis) and of the gastrointestinal apparatus (e.g. Crohn's disease). However, IL-23 also exerts a role in promoting tumour incidence and growth. In point of fact, IL-23 regulates a series of circuits in the tumoral microenvironment, stimulating angiogenesis and the production of inflammation mediators.

Psoriasis is a chronic inflammatory skin disease that affects 3% of the world's population (Koo J. Dermatol. Clin. 1996; 14:485-96; Schon M. P. et al., N. Engl. J. Med. 2005; 352: 1899-912). A type-1 aberrant immune response has been correlated with the pathogenesis of psoriasis, and the cytokines that induce this response, such as IL-12 and IL-23, may represent suitable therapeutic objects. The expression of IL-12 and IL-23, which share the subunit p40, is significantly increased in psoriasis plaques, and preclinical studies have demonstrated a role of these cytokines in the pathogenesis of psoriasis. More recently, the treatment of anti-IL-12 and IL-23 monoclonal antibodies of patients suffering from psoriasis proved to be effective in improving the signs of progression and seriousness of the disease and has subsequently reinforced the role of IL-12 and IL-23 in the physiopathology of psoriasis.

Crohn's disease is a chronic inflammatory pathology of the digestive apparatus and may affect any region thereof—from the mouth to the anus. It typically afflicts the terminal tract of the ileum and well-defined areas of the large intestine. It is often associated with systemic autoimmune disorders, such as mouth ulcers and rheumatic arthritis. Crohn's disease affects over 500 000 people in Europe and 600 000 people in the United States.

Crohn's disease is a pathology associated with a Th1 cell-mediated excessive activity of cytokines. IL-12 is a key cytokine in the initiation of the inflammatory response mediated by Th1 cells. Crohn's disease is characterized by increased production of IL-12 by cells presenting the antigen in intestinal tissue, and of gamma-interferon (IFN-$\gamma$) and TNF$\alpha$ by lymphocytes and intestinal macrophages. These cytokines induce and support the inflammatory process and thickening of the intestinal wall, which are characteristic signs of the pathology. Preclinical and clinical evidence has demonstrated that inhibition of IL-12 is effective in controlling the inflammatory response in models of intestinal inflammation and/or in patients suffering from Crohn's disease.

The relationship between cancer and inflammation is now an established fact. Many forms of tumours originate from sites of inflammation, and inflammation mediators are often produced in tumours.

IL-23 has been identified as a cytokine associated with cancer and, in particular, the expression of IL-23 is significantly high in samples of human carcinomas when compared with normal adjacent tissues. In addition, the absence of a significant expression of IL-23 in the normal adjacent tissues suggests an over-regulation of IL-23 in tumours, reinforcing its role in tumour genesis.

European patent EP-B-0 382 276 describes a number of 1-benzyl-3-hydroxymethylindazole derivatives endowed with analgesic activity. In turn, European patent EP-B-0 510 748 describes, on the other hand, the use of these derivatives for preparing a pharmaceutical composition that is active in the treatment of autoimmune diseases. Finally, European patent EP-B-1 005 332 describes the use of these derivatives for preparing a pharmaceutical composition that is active in treating diseases derived from the production of MCP-1. 2-Methyl-2-{[1-(phenylmethyl)-1H-indazol-3-yl]methoxy}propanoic acid is thought to be capable of inhibiting, in a dose-dependent manner, the production of MCP-1 and TNF-$\alpha$ induced in vitro in monocytes from LPS and *Candida albicans*, whereas the same compound showed no effects in the production of cytokines IL-1 and IL-6, and of chemokines IL-8, MIP-1$\alpha$, and RANTES (Sironi M. et al., "A small synthetic molecule capable of preferentially inhibiting the production of the CC chemokine monocyte chemotactic protein-1", European Cytokine Network. Vol. 10, No. 3, 437-41, September 1999).

European patent application EP-A-1 185 528 relates to the use of triazine derivatives for inhibiting the production of IL-12. European patent application EP-A-1 188 438 and EP- A-1 199 074 relate to the use of inhibitors of the enzyme PDE4, for instance Rolipram, Ariflo and diazepine-indole derivatives, in the treatment and prevention of diseases associated with excessive production of IL-12. European patent application EP-A-1 369 119 relates to the use of hyaluronane with a molecular weight of between 600 000 and 3 000 000 daltons for controlling and inhibiting the expression of IL-12. European patent application EP-A-1 458 687 relates to the use of pyrimidine derivatives for treating diseases related to an overproduction of IL-12. European patent application EP-A-1 819 341 relates to the use of nitrogenous heterocyclic compounds, for instance pyridine, pyrimidine and triazine derivatives, for inhibiting the production of IL-12 (or of other cytokines, such as IL-23 and IL-27 which stimulate the production of IL-12). European patent application EP-A-1 827 447 relates to the use of pyrimidine derivatives for treating diseases related to an overproduction of IL-12, IL-23 and IL-27.

European patent applications EP-A-1 869 055, EP-A-1 869 056 and EP-A-1 675 862 describe 1,3-thiazolo-4,5-pyrimidine derivatives that are capable of acting as CX3CR1 receptor antagonists.

Despite the activity developed thus far, there is still felt to be a need for novel pharmaceutical compositions and compounds that are effective in the treatment of diseases based on the expression of MCP-1, CX3CR1 and p40.

The Applicant has found, surprisingly, novel 1-benzyl-3-hydroxymethylindazole derivatives with pharmacological activity.

The Applicant has found, surprisingly, that the novel 1-benzyl-3-hydroxymethylindazole derivatives according to formula (I) of the present invention are capable of reducing the production of the chemokine MCP-1.

More surprisingly, the Applicant has found that the novel 1-benzyl-3-hydroxymethylindazole derivatives according to formula (I) of the present invention are capable of reducing the expression of the chemokine MCP-1.

Even more surprisingly, the Applicant has found that the 1-benzyl-3-hydroxymethylindazole derivatives according to formula (I) of the present invention are capable of reducing the expression of the subunit p40 involved in the production of the cytokines IL-12 and IL-23, and the expression of the receptor CX3CR1.

Thus, in a first aspect, the present invention consists of a compound of formula (I)

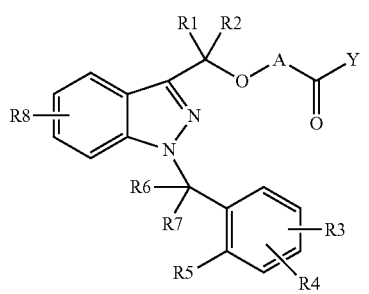

in which:
A may be —$X_1$— or —$X_1$—OC($R_9$)($R_{10}$)—, in which
$X_1$ may be an alkyl group having from 1 to 5 carbon atoms, optionally substituted with one or more alkyl groups having from 1 to 5 carbon atoms or one or more alkoxy groups having from 1 to 3 carbon atoms, and $R_9$ and $R_{10}$, which may be identical or different each other, may be hydrogen, an alkyl group having from 1 to 5 carbon atoms or an alkoxy group having from 1 to 3 carbon atoms, Y is OH $R_1$ and $R_2$, which may be identical or different each other, may be hydrogen, an alkyl group having from 1 to 5 carbon atoms or an alkoxy group having from 1 to 3 carbon atoms, $R_3$, $R_4$ and $R_8$, which may be identical or different each other, may be hydrogen, an alkyl group having from 1 to 5 carbon atoms, an alkoxy group having from 1 to 3 carbon atoms, a halogen atom, —OH, —N(R')(R''), —N(R')COR'', —CN, —CONR'R'', —SO$_2$NR'R'', —SO$_2$R', nitro and trifluoromethyl; with R' and R'', which may be identical or different each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, —OH, —N(R')(R''), —N(R')COR'', nitro and trifluoromethyl, or $R_5$ together with one from between $R_6$ and $R_7$ forms a ring having 5 or 6 carbon atoms; with R' and R'', which may be identical or different each other, represented by hydrogen and an alkyl group having from 1 to 5 carbon atoms, $R_6$ and $R_7$, which may be identical or different each other, may be hydrogen, an alkyl group having from 1 to 5 carbon atoms, or together form a group C=O, or one from between $R_6$ and $R_7$, together with $R_5$, forms a ring having 5 or 6 carbon atoms, with the proviso that when Y is —OH, A is different from an alkyl group having 1 carbon atom, optionally substituted with one or more alkyl groups having from 1 to 5 carbon atoms, or alternatively at least one of the groups from $R_1$ to $R_8$ is different from hydrogen.

In a second aspect, the present invention relates to a pharmaceutical composition comprising the novel 1-benzyl-3-hydroxymethylindazole derivatives according to formula (I) or a pharmaceutically acceptable salt thereof together with at least one pharmaceutically acceptable vehicle.

The over-regulation and/or the increase of the expression of the above mentioned MCP-1, CX3CR1, and p40, the latest resulting consequently in IL-12 and/or IL-23 expression/production, which results in a development of a pathology and/or a disease is often referred in the art with the term "overexpression". For the purpose of the present invention, the term expression is intended to include overexpression as known in the art.

Surprisingly, the Applicant has found that the novel 1-benzyl-3-hydroxymethylindazole derivatives may be used for the preparation of a pharmaceutical composition that is active in the case of diseases based on the expression of the chemokine MCP-1, of the subunit p40, and consequently of the cytokines IL-12 and IL-23, and of the receptor CX3CR1.

More surprisingly, the Applicant has also found that a number of known 1-benzyl-3-hydroxymethylindazole derivatives may be used for preparing a pharmaceutical composition that is active in the treatment of diseases based on the expression of the subunit p40, and consequently of the cytokines IL-12 and IL-23, and of the receptor CX3CR1.

Thus, in a further aspect, the present invention relates to the use of a compound of formula (I)

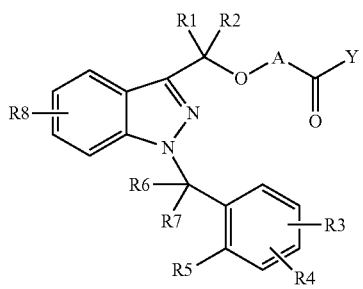

(I)

in which:

A may be —$X_1$— or —$X_1$—OC($R_9$)($R_{10}$)—, in which $X_1$ may be an alkyl group having from 1 to 5 carbon atoms, optionally substituted with one or more alkyl groups having from 1 to 5 carbon atoms or one or more alkoxy groups having from 1 to 3 carbon atoms, and $R_9$ and $R_{10}$, which may be identical or different each other, may be hydrogen, an alkyl group having from 1 to 5 carbon atoms or an alkoxy group having from 1 to 3 carbon atoms, Y is OH, $R_1$ and $R_2$, which may be identical or different each other, may be hydrogen, an alkyl group having from 1 to 5 carbon atoms or an alkoxy group having from 1 to 3 carbon atoms, $R_3$, $R_4$ and $R_8$, which may be identical or different each other, may be hydrogen, an alkyl group having from 1 to 5 carbon atoms, an alkoxy group having from 1 to 3 carbon atoms, a halogen atom, —OH, —N(R')(R''), —N(R')COR'', —CN, —CONR'R'', —$SO_2$NR'R'', —$SO_2$R', nitro and trifluoromethyl; with R' and R'', which may be identical or different each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, —OH, —N(R')(R''), —N(R')COR'', nitro and trifluoromethyl, or $R_5$ together with one from among $R_6$ and $R_7$ forms a ring having 5 or 6 carbon atoms; with R' and R'', which may be identical or different each other, represented by hydrogen and an alkyl group having from 1 to 5 carbon atoms, and $R_6$ and $R_7$, which may be identical or different each other, may be hydrogen, an alkyl group having from 1 to 5 carbon atoms, or together form a group C=O, or one from among $R_6$ and $R_7$, together with $R_5$, forms a ring having 5 or 6 carbon atoms, for preparing a pharmaceutical composition for the treatment of diseases based on the expression of CX3CR1 and p40, or with the proviso that when Y is —OH, A is different from an alkyl group containing 1 carbon atom, optionally substituted with one or more alkyl groups containing from 1 to 5 carbon atoms, or alternatively at least one of the groups from $R_1$ to $R_8$ is different from hydrogen, for preparing a pharmaceutical composition for the treatment of diseases based on the expression of MCP-1.

In addition, in a further aspect, the present invention relates to a method for treating or preventing diseases based on the expression of MCP-1, CX3CR1 and p40, characterized by the administration to a person in need thereof an effective amount of the compound of formula (I) previously described.

DETAILED DESCRIPTION OF THE INVENTION

Preferably, in formula (I) previously described, residue A is represented by the group $X_1$ or $X_1$—OC($R_9$)($R_{10}$), where $X_1$ is an alkyl group having from 1 to 3 carbon atoms, optionally substituted with one or more alkyl groups having from 1 to 3 carbon atoms or one or more alkoxy groups having 1 or 2 carbon atoms, and $R_9$ and $R_{10}$, which may be identical or different each other, are hydrogen, an alkyl group having from 1 to 3 carbon atoms or an alkoxy group having 1 or 2 carbon atoms.

More preferably, residue A is represented by the group $X_1$ or $X_1$—OC($R_9$)($R_{10}$), where $X_1$ is the group $CH_2$, the group $CH_2CH_2$ or the group $C(CH_3)_2$, and $R_9$ and $R_{10}$, which may be identical or different each other, are hydrogen or a $CH_3$ group.

Advantageously, residue A is chosen from the group comprising a group $CH_2$, a group $CH_2CH_2$, a group $C(CH_3)_2$, a group $CH_2CH_2OCH_2$, a group $CH_2CH_2OC(CH_3)_2$ and a group $CH_2CH_2CH_2OC(CH_3)_2$.

Preferably, $R_1$ and $R_2$, which may be identical or different each other, are represented by a hydrogen atom, an alkyl group having from 1 to 3 carbon atoms or an alkoxy group having 1 or 2 carbon atoms.

Preferably, $R_3$, $R_4$ and $R_8$, which may be identical or different each other, are represented by a hydrogen atom, an alkyl group having from 1 to 3 carbon atoms, an alkoxy group having 1 or 2 carbon atoms, a Br, Cl or F atom, an OH group, a nitro group, a trifluoromethyl group or a group N(R')(R'') or N(R')COR''; —CN, —CONR'R'', —$SO_2$NR'R'', —$SO_2$R', with R' and R'', which may be identical or different each other, represented by a hydrogen atom and an alkyl group having from 1 to 3 carbon atoms.

Advantageously, $R_5$ is represented by a hydrogen atom, an alkyl group having from 1 to 3 carbon atoms, an alkoxy group having 1 or 2 carbon atoms, a halogen atom, an OH group, or $R_5$, together with one from among $R_6$ and $R_7$, forms a ring having 5 or 6 carbon atoms.

Preferably, $R_6$ and $R_7$, which may be identical or different each other, are represented by a hydrogen atom, an alkyl group having from 1 to 3 carbon atoms, or together form a group C=O, or one from among $R_6$ and $R_7$, together with $R_5$, forms a ring having 5 or 6 carbon atoms.

In the case of certain substituents, the compound of formula (I) according to the present invention may be an asymmetric carbon atom and may then be in the form of stereoisomers and enantiomers.

Depending on the nature of the substituents, the compound of formula (I) may form addition salts with physiologically acceptable organic or mineral acids or bases.

Typical examples of suitable physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable mineral bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

Depending on the nature of the substituents, the compound of formula (I) may form esters with physiologically acceptable organic acids or bases.

The compounds of the present invention also include the prodrugs, stereoisomers, enantiomers and pharmaceutically acceptable salts or esters of the compounds represented by formula (I) described in the claims. The prodrug of a compound of formula (I) is a substance in substantially inactive form, which, when administered to a living being, is metabolized into a compound of formula (I).

The terms "pharmaceutically acceptable" and "physiologically acceptable" are intended to define, without any particular limitation, any material suitable for preparing a pharmaceutical composition to be administered to a living being.

The compounds according to formula (I) of the present invention may be used for the preparation of a pharmaceutical composition that is active in the treatment of diseases (or pathologies) based on the expression of the chemokine MCP-1, the cytokine p40, the subunit p40 (involved in the production of cytokines IL-12 and IL-23) and the receptor CX3CR1.

Preferably, the pathologies associated with the expression of MCP-1 and CX3CR1 are articular diseases, renal diseases, cardiovascular diseases, metabolic syndrome, obesity, diabetes, insulin resistance and cancer.

In particular, the pathologies associated with the expression of MCP-1 are rheumatoid arthritis, arthritis induced by viral infections, psoriatic arthritis, arthrosis, lupus nephritis, diabetic nephropathy, glomerulonephritis, polycystic kidney disease, interstitial lung disease, fibrosis, multiple sclerosis, Alzheimer's disease, HIV-associated dementia, atopic dermatitis, psoriasis, vasculitis, restenosis, atherosclerosis, myocardial infarction, angina, acute coronary diseases, adenomas, carcinomas and metastases, metabolic diseases and complications following surgical interventions such as, for example, angioplasty, arterectomy, circulation recovery techniques, transplants, organ replacements, tissue replacements and prosthesis implants.

In particular, the pathologies associated with the expression of CX3CR1 are rheumatoid arthritis, lupus nephritis, diabetic nephropathy, Crohn's disease, ulcerative colitis, coronary disorders, restenosis, atherosclerosis, myocardial infarction, angina, and complications following surgical interventions such as, for example, angioplasty, arterectomy and circulation recovery techniques.

Preferably, the pathologies associated with the expression of p40, and thus of IL-12 and IL-23, are autoimmune diseases, such as chronic degenerative inflammatory diseases, and cancer.

In particular, the pathologies associated with the expression of p40 are rheumatoid arthritis, psoriasis, glomerulonephritis, diabetes, lupus erythematosus, diabetes, Crohn's disease, and tumours such as, for example, colon carcinomas, breast carcinomas, lung carcinomas and prostate carcinomas, and skin and CNS neoplasias.

Preferably, the pharmaceutical compositions of the present invention are prepared in suitable dosage forms comprising an effective dose of at least one compound of formula (I), or a pharmaceutically acceptable salt, ester or prodrug thereof, and at least one pharmaceutically acceptable vehicle.

Examples of pharmaceutically acceptable vehicles known in the prior art are, for example, glidants, binders, disintegrants, fillers, diluents, flavourings, colorants, fluidizers, lubricants, preserving agents, humectants, absorbents and sweeteners.

Useful examples of pharmaceutically acceptable excipients are sugars, such as lactose, glucose or sucrose, starches, such as corn starch and potato starch, cellulose and derivatives thereof, for instance sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols such as propylene glycol, polyols such as glycerol, sorbitol, mannitol and polyethylene glycol, esters such as ethyl oleate and ethyl laurate, agar-agar, and the like.

Examples of suitable dosage forms are tablets, capsules, coated tablets, granules, solutions and syrups for oral administration; medicated plasters, solutions, pastes, creams and ointments for transdermal administration; suppositories for rectal administration and sterile solutions for injection or aerosol administration.

Other suitable dosage forms are sustained-release forms and liposome-based forms, for either the oral or injection route.

The dosage forms may also contain other conventional ingredients such as: preserving agents, stabilizers, surfactants, buffers, osmotic pressure regulators, emulsifiers, sweeteners, colorants, flavourings and the like.

When required for particular therapies, the pharmaceutical composition of the present invention may contain other pharmacologically active ingredients whose simultaneous administration is useful.

The amount of compound of formula (I) or of pharmaceutically acceptable salt, ester or prodrug thereof in the pharmaceutical composition of the present invention may vary within a wide range as a function of known factors, for instance the type of pathology to be treated, the severity of the disease, the body weight of the patient, the dosage form, the chosen route of administration, the number of daily administrations and the efficacy of the chosen compound of formula (I). However, the optimum amount may be determined simply and routinely by a person skilled in the art.

Typically, the amount of compound of formula (I) or of pharmaceutically acceptable salt, ester or prodrug thereof in the pharmaceutical composition of the present invention will be such that it ensures a level of administration of between 0.001 and 100 mg/kg/day. Preferably, the level of administration is between 0.05 and 50 mg/kg/day and even more preferably between 0.1 and 10 mg/kg/day.

The dosage forms of the pharmaceutical composition of the present invention may be prepared according to techniques that are well known to pharmaceutical chemists, including mixing, granulation, compression, dissolution, sterilization and the like.

The activity of the compounds of the present invention on MCP-1 and CX3CR1 was demonstrated in vitro in human monocytes via techniques of gene expression analysis with "real-time" RT-PCR and by protein production analysis via an immunoenzymatic test. As is known to those skilled in the art, the abovementioned experimental models are considered useful for checking the activity of the compounds with regard to the expression and production of MCP-1 and the expression of CX3CR1. Consequently, the abovementioned models may be considered as predictive of the activity in man for the treatment of pathologies characterized by the expression and production of MCP-1, by the expression of CX3CR1 and by inflammatory conditions with the presence of infiltrates rich in monocytes and macrophages.

The activity of the compounds of the present invention on p40 was demonstrated in vitro in human monocytes via gene expression analysis techniques via "real-time" RT-PCR. As is known to those skilled in the art, the abovementioned experimental model is useful for checking the activity of compounds with regard to the expression of p40 and may be considered as predictive of the activity in man for the treatment of pathologies characterized by the expression of p40.

The preparation of the compounds of general formula (I) may be performed according to one of the following procedures.

Method A:

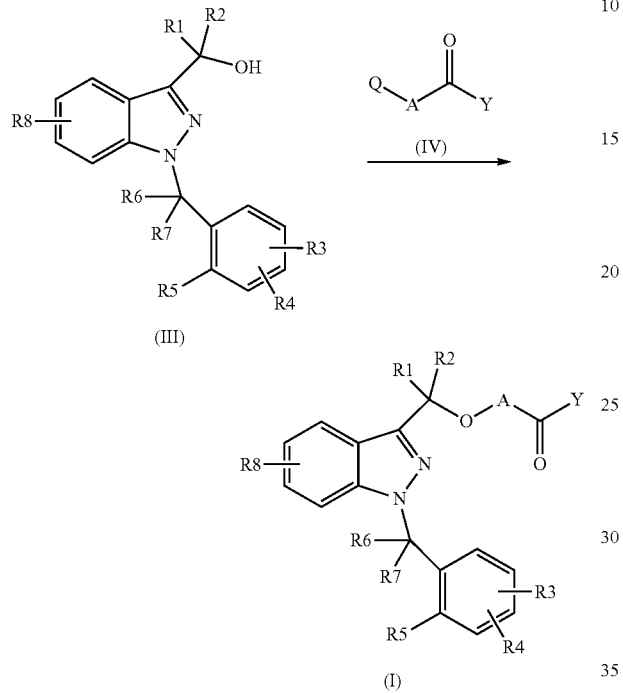

Method B:

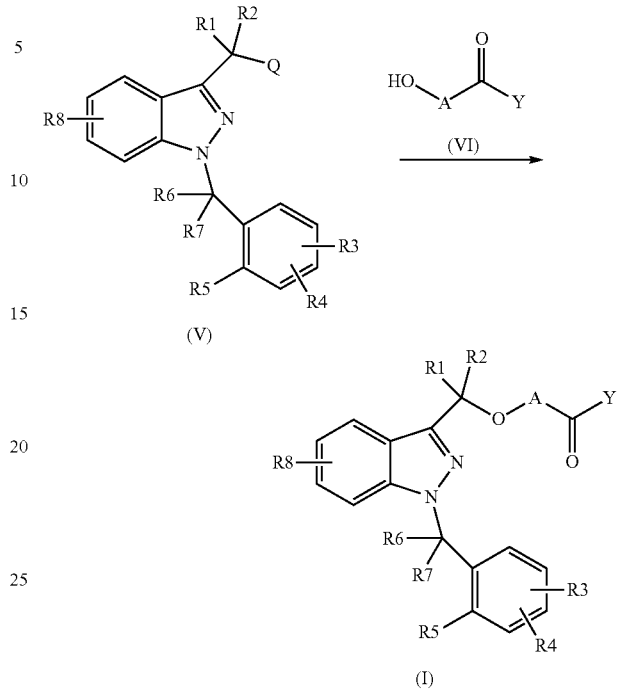

In method A, the compounds of general formula (III) are reacted with the compounds of formula (IV). The substituents $R_1$ to $R_8$, A and Y have the meanings given previously for the compounds of formula (I) and Q indicates a leaving group chosen from the group comprising halogen, $CH_3SO_3$— and $p$-$CH_3PhSO_3$—.

Method A is performed according to conventional techniques. For example, the alcohols of formula (III) are reacted, respectively, with the derivatives of formula (IV) in which Q is a leaving group preferably chosen from the group comprising a chlorine atom, a bromine atom and a methanesulfonyl group. The reaction is performed in the presence of a suitable base and in a suitable solvent. The bases that may preferably be used are NaH, butyl lithium and lithium diisopropylamide, whereas the solvents that are suitable for this type of reaction are preferably polar aprotic solvents such as tetrahydrofuran, diethyl ether or 1,4-dioxane. The reaction temperature is preferably between room temperature and the reflux temperature of the solvent used. Reactions of this type may last from a few hours to a few days.

In method B, the compounds of general formula (V) are reacted with the compounds of formula (VI). The substituents $R_1$ to $R_8$, A and Y have the meanings given previously for the compounds of formula (I) and Q indicates a leaving group chosen from the group comprising halogen, $CH_3SO_3$— and $p$-$CH_3PhSO_3$—.

Method B is performed according to conventional techniques. For example, the alcohols of formula (VI) are reacted, respectively, with the derivatives of formula (V) in which Q is a leaving group preferably chosen from the group comprising a chlorine atom, a bromine atom and a methanesulfonyl group. The reaction is performed in the presence of a suitable base and in a suitable solvent. The bases that may preferably be used are NaH, butyl lithium and lithium diisopropylamide, whereas the solvents that are suitable for this type of reaction are preferably polar aprotic solvents such as tetrahydrofuran, diethyl ether or 1,4-dioxane. The reaction temperature is preferably between room temperature and the reflux temperature of the solvent used. Reactions of this type may last from a few hours to a few days.

The examples that follow are intended to illustrate the present invention without, however, limiting it in any way.

Preparative Examples

The compounds of formula (I) listed in Table A below were prepared using the preparation methods described previously.

TABLE A

| | | | | | Groups R | | | | | |
|---|---|---|---|---|---|---|---|---|---|---|
| No. | A | Y | 1 | 2 | 3 | 4 | 5 | 6 | 7 | 8 |
| 1 | C(CH₃)₂ | OH | H | H | p-OMe | H | H | H | H | H |
| 2 | " | " | " | " | H | " | " | " | " | 5-OMe |
| 3 | " | " | " | " | " | " | " | C=O | | H |
| 4 | " | " | " | " | " | p-Cl | " | " | H | H | " |

TABLE A-continued

| | | | Groups R | | | | | | | |
|---|---|---|---|---|---|---|---|---|---|---|
| No. | A | Y | 1 | 2 | 3 | 4 | 5 | 6 | 7 | 8 |
| 5 | " | " | " | " | H | " | " | " | " | 5-Cl |
| 6 | " | " | " | " | " | " | " | " | " | 5-NO$_2$ |
| 7 | " | " | " | " | p-Cl | m-Cl | " | " | " | H |
| 8 | " | " | " | " | H | H | (CH$_2$)$_3$ | " | " | " |
| 17 | CH$_2$ | " | " | " | p-F | " | H | H | " | " |
| 18 | " | " | " | " | p-Cl | o-Cl | " | " | " | " |
| 19 | CH$_2$CH$_2$OCH$_2$ | " | " | " | H | H | " | " | " | " |
| 20 | (CH$_2$)$_2$OC(CH$_3$)$_2$ | " | " | " | " | " | " | " | " | " |
| 21 | (CH$_2$)$_3$OC(CH$_3$)$_2$ | " | " | " | " | " | " | " | " | " |
| 22 | C(CH$_3$)$_2$ | " | " | " | p-CH$_3$ | " | " | " | " | " |
| 23 | " | " | " | " | H | " | " | " | " | 5-Br |
| 24 | " | " | " | " | " | " | " | " | " | 5-NH$_2$ |
| 25 | CH$_2$ | " | " | " | p-Cl | o-Me | " | " | " | H |
| 29 | C(CH$_3$)$_2$ | " | " | " | H | H | " | " | " | " |
| 30 | " | " | " | " | " | " | " | " | " | 5-CN |
| 31 | " | " | " | " | " | " | " | " | " | 5-CONH$_2$ |
| 32 | " | " | " | " | " | " | " | " | " | 5-SO$_2$NH$_2$ |
| 33 | (CH$_2$)$_3$OCH$_2$ | " | " | " | " | " | " | " | " | H |
| 34 | C(CH$_3$)$_2$CH$_2$OCH$_2$ | " | " | " | " | " | " | " | " | " |

The details of the preparation of most compounds of Table A are given hereinbelow. The remaining compounds were prepared with similar techniques using suitable starting products and reagents.

Preparation of Compound 1

2-{[1-(4-methoxybenzyl)-1H-indazol-3-yl]methoxy}-2-methylpropanoic acid

1a) [1-(4-methoxybenzyl)-1H-indazol-3-yl]methanol

To a suspension of 60% NaH (2.7 g; 0.07 mol) in toluene (200 ml) was added 1-benzyl-3-hydroxymethylindazole (10 g; 0.07 mol). The mixture was brought to the boiling point and left stirring at reflux for 1 hour. 4-Methoxybenzyl chloride (14 g; 0.09 mol) was then added. The mixture was then stirred at reflux for 4 hours. The reaction was stopped by cooling the mixture to room temperature and adding water (50 ml). The organic phase was separated out and washed, respectively, with 2N HCl (50 ml) and water (5×50 ml). The solvent was evaporated off under reduced pressure. The crude residue thus obtained was purified by flash chromatography on silica gel, using as eluent a 3/2 hexane/ethyl acetate mixture. The product obtained was crystallized from a 5/1 hexane/ethyl acetate mixture to give 5.1 g of [1-(4-methoxybenzyl)-1H-indazol-3-yl]methanol with a melting point of 95-97° C.

$^1$H-NMR (CDCl$_3$, δ ppm): 3.43 (t, J=6.9 Hz, 1H), 3.67 (s, 3H), 4.98 (d, J=6.9 Hz, 2H), 5.36 (s, 2H), 6.5-6.8 (m, 2H), 6.9-7.4 (m, 7H), 7.80 (d, J=7.86 Hz, 1H).

1b) 2-{[1-(4-methoxybenzyl)-1H-indazol-3-yl]methoxy}-2-methylpropanoic acid

To a suspension of NaOH (15.6 g; 0.39 mol) in acetone (50 ml) was added [1-(4-methoxybenzyl)-1H-indazol-3-yl]methanol (8.7 g; 0.03 mol). To the mixture was slowly added a solution of chloroform (7.2 ml; 0.09 mol) and acetone (7.2 ml; 0.1 mol). The addition caused refluxing of the mixture of solvents. Once the addition was complete, the mixture was refluxed for 1 hour. The reaction was stopped by cooling the mixture to room temperature and evaporating off the solvent under reduced pressure. The resulting crude residue was taken up in toluene (100 ml) and water (50 ml). The aqueous phase was separated from the organic phase and then washed with toluene (2×50 ml). The combined organic phases were extracted with water (3×50 ml). The combined aqueous phases were washed with hexane (2×30 ml) and then acidified with 2N HCl and stirred at room temperature. The solid thus obtained was filtered off and crystallized first from a 5/1 water/acetic acid mixture, and then from toluene, to give 4.8 g of 2-{[1-(4-methoxybenzyl)-1H-indazol-3-yl]methoxy}-2-methylpropanoic acid with a melting point of 169-171° C.

$^1$H-NMR (DMSO-d6, δ ppm): 1.44 (s, 6H), 3.69 (s, 3H), 4.74 (s, 2H), 5.52 (s, 2H), 6.82-6.90 (m, 2H), 7.13 (t, J=7.50 Hz, 1H), 7.18-7.26 (m, 2H), 7.36 (t, J=7.23 Hz, 1H), 7.66 (d, J=8.42 Hz, 1H), 7.92 (dd, J=8.14; 1.01 Hz, 1H), 12.76 (s, 1H).

Preparation of Compound 2

2-[(1-benzyl-5-methoxy-1H-indazol-3-yl)methoxy]-2-methylpropanoic acid 2a) benzyl 1-benzyl-5-methoxy-1H-indazole-3-carboxylate A suspension of 5-methoxy-1H-indazole-3-carboxylic acid (21.5 g; 0.11 mol) and 60% NaH (10.5 g; 0.44 mol) in N,N-dimethylformamide (DMF) (200 ml) was stirred at 70° C. for 1 hour. Benzyl chloride (32.9 g; 0.26 mol) was then added slowly to the suspension and the mixture was stirred at 70° C. for 4 hours. The reaction was stopped by cooling the mixture to room temperature and pouring the mixture into water and ice. The product was extracted with ethyl acetate (3×250 ml). The combined organic phases were concentrated under reduced pressure. The crude residue thus obtained was purified by successive crystallizations from 95° ethanol, to give 18 g of benzyl 1-benzyl-5-methoxy-1H-indazole-3-carboxylate with a melting point of 107-109° C.

$^1$H-NMR (CDCl$_3$, δ ppm): 3.78 (s, 3H), 5.51 (s, 2H), 6.9-7.6 (m, 13H).

2b) (1-benzyl-5-methoxy-1H-indazol-3-yl)methanol

To a solution of benzyl 1-benzyl-5-methoxy-1H-indazole-3-carboxylate (17.7 g; 0.05 mol), diethyl ether (100 ml) and tetrahydrofuran (THF) (170 ml) stirred at room temperature was slowly added LiAlH$_4$ (3.8 g; 0.1 mol). Once the addition was complete, the suspension was stirred at reflux for 24 hours. The reaction was stopped by destroying the excess LiAlH$_4$ via addition of water (40 ml) and 5N NaOH (10 ml). The organic phase was separated out and the solvent was evaporated off under reduced pressure. The crude residue obtained was purified by crystallization from 95° ethanol to give 14 g of (1-benzyl-5-methoxy-1H-indazol-3-yl)methanol with a melting point of 97-98° C.

$^1$H-NMR (CDCl$_3$, δ ppm): 3.3 (bs, 1H), 3.80 (s, 3H), 4.92 (s, 2H), 5.47 (s, 2H), 6.9-7.5 (m, 8H).

2c)
1-benzyl-3-(chloromethyl)-5-methoxy-1H-indazole

To a solution of (1-benzyl-5-methoxy-1H-indazol-3-yl) methanol (18 g; 0.07 mol) in chloroform (200 ml) stirred at room temperature was slowly added thionyl chloride (15.8 g; 0.13 mol). Once the addition was complete, the solution was refluxed for 24 hours. The reaction was then stopped by cooling the mixture to room temperature and evaporating off the solvent under reduced pressure. The residue was then taken up several times in toluene and concentrated under reduced pressure. The crude residue obtained was purified by crystallization from hexane to give 9.5 g of 1-benzyl-3-(chloromethyl)-5-methoxy-1H-indazole with a melting point of 78-80° C.

$^1$H-NMR (CDCl$_3$, δ ppm): 3.85 (s, 3H), 4.97 (s, 2H), 5.51 (s, 2H), 6.9-7.4 (m, 8H).

2d) 2-[(1-benzyl-5-methoxy-1H-indazol-3-yl)methoxy]-2-methylpropanoic acid

To a solution containing 1-benzyl-3-(chloromethyl)-5-methoxy-1H-indazole (2.95 g; 0.01 mol) and ethyl 3-hydroxy-3-methylbutanoate (1.98 g; 0.015 mol) in DMF (30 ml) stirred at room temperature was slowly added 60% NaH (0.36 g; 0.015 mol). The mixture was then heated at 40° C. for 24 hours. The reaction was stopped by cooling the suspension to room temperature and adding water (200 ml). The solvent was evaporated off under reduced pressure and the residue was treated at reflux with NaOH (0.84 g; 0.021 mol) in water (6 ml) and 95° ethanol (6 ml) for 6 hours. The mixture was then cooled to room temperature and diluted with water (50 ml). The alkaline phase was washed with diethyl ether (2×20 ml) and then acidified with concentrated HCl and extracted with diethyl ether (3×30 ml).

The combined organic phases were concentrated under reduced pressure and the crude residue obtained was purified by crystallization from 10/1 hexane/ethyl acetate mixture to give 0.8 g of 2-[(1-benzyl-5-methoxy-1H-indazol-3-yl)methoxy]-2-methylpropanoic acid with a melting point of 128-130° C.

$^1$H-NMR (DMSO-d6, δ ppm): 1.44 (s, 6H), 3.77 (s, 3H), 4.69 (s, 2H), 5.55 (s, 2H), 7.02 (dd, J=9.15; 2.38 Hz, 1H), 7.17-7.33 (m, 5H), 7.41 (d, J=2.38 Hz, 1H), 7.55 (d, J=9.15 Hz, 1H), 12.79 (s, 1H).

Preparation of Compound 3

2-[(1-benzoyl-1H-indazol-3-yl)methoxy]-2-methylpropanoic acid 3a) (1-tritylindazol-3-yl)methanol To a solution containing isobutyl 1H-indazole-3-carboxylate (280 g; 1.28 mol) in chloroform (2 L) stirred at room temperature were added triethylamine (300 ml; 2.16 mol) and triphenylchloromethane (400 g; 1.4 mol). The solution was stirred at room temperature for 4 days, and water (500 ml) was then added. The organic phase was separated out and concentrated under reduced pressure. The crude residue obtained was used without further purification in the following step.

To a solution of the crude isobutyl 1-tritylindazole-3-carboxylate (180 g; 0.39 mol) in THF (1 L) stirred at room temperature was added slowly a suspension of LiAlH$_4$ (18 g; 0.48 mol) in THF (100 ml). Once the addition was complete, the mixture was stirred at room temperature for 30 minutes, and the reaction was then stopped by cooling the mixture to 0° C. and successively adding water (40 ml), 2N NaOH (40 ml) and water (60 ml). The solid thus formed was filtered off and the solution was concentrated under reduced pressure. The crude residue obtained was purified by crystallization from a 1/1 hexane/ethyl acetate mixture. 120 g of (1-tritylindazol-3-yl)methanol were obtained.

m.p.=192-193° C.

$^1$H-NMR (CDCl$_3$; δ ppm): 2.51 (t, J=6.98 Hz, 1H), 4.90 (d, J=6.98 Hz, 2H), 6.2-6.5 (m, 1H), 6.9-7.4 (m, 17H), 7.6-7.8 (m, 1H).

3b)
2-(1-tritylindazol-3-ylmethoxy)-2-methylpropanoic acid

To a suspension of (1-tritylindazol-3-yl)methanol (78 g; 0.20 mol), acetone (260 ml) and water (0.5 ml) stirred at room temperature were added NaOH (76 g; 1.9 mol) and, slowly, a 1/1 chloroform/acetone mixture (100 ml). The reaction is exothermic and the rate of addition was adjusted so as to keep the reaction temperature close to the boiling point. 30 minutes after the end of addition, the reaction was stopped by cooling the mixture to room temperature and evaporating off the solvent under reduced pressure. The residue was taken up in water (500 ml) and washed with diethyl ether (3×100 ml). The aqueous phase was then acidified with concentrated HCl and the product was extracted with toluene (3×250 ml). The combined organic phases were concentrated under reduced pressure and the crude residue obtained was purified by crystallization from a 3/7 hexane/ethyl acetate mixture to give 22 g of 2-(1-tritylindazol-3-ylmethoxy)-2-methylpropanoic acid, m.p.=179-180° C.

$^1$H-NMR (CDCl$_3$, δ ppm): 1.53 (s, 6H), 4.88 (s, 2H), 6.3-6.5 (m, 1H), 6.9-7.5 (m, 17H), 7.8-8.0 (m, 1H), 9.3 (bs, 1H).

3c) 2-(1H-indazol-3-ylmethoxy)-2-methylpropanoic acid

To a solution of 2-(1-tritylindazol-3-ylmethoxy)-2-methylpropanoic acid (83 g; 0.174 mol) in dichloromethane (DCM) (900 ml) stirred at room temperature was added para-toluenesulfonic acid (PTSA) (50 g; 0.29 mol). The mixture was stirred for 30 minutes at room temperature and then poured into 5N NaOH (400 ml). The organic phase was separated out and washed with water (300 ml). The combined aqueous phases were acidified with concentrated HCl and then extracted with ethyl acetate (5×300 ml). The combined organic phases were evaporated under reduced pressure and the resulting crude residue was purified by crystallization from a 1/1 hexane/ethyl acetate mixture.

42 g of 2-(1H-indazol-3-ylmethoxy)-2-methylpropanoic acid were obtained, m.p.=135-137° C.

$^1$H-NMR (DMSO-d6, δ ppm): 1.46 (s, 6H), 4.77 (s, 2H), 7.0-7.6 (m, 3H), 7.94 (d, J=7.88 Hz, 1H).

3d) 2-[(1-benzoyl-1H-indazol-3-yl)methoxy]-2-methylpropanoic acid

To a solution of 2-(1H-indazol-3-ylmethoxy)-2-methylpropanoic acid (6 g; 0.026 mol) in acetone (50 ml) stirred at room temperature was added $K_2CO_3$ (6.8 g; 0.049 mol) and then, slowly, a solution of benzoyl chloride (5 ml; 0.043 mol) in acetone (30 ml). The mixture was stirred at room temperature for 24 hours and then poured into water (1 L). The solution was then brought to basic pH with 5N NaOH and washed with diethyl ether (3×150 ml). The alkaline phase was then acidified with concentrated HCl and extracted with diethyl ether (3×300 ml). The combined organic phases were concentrated under reduced pressure and the crude residue obtained was purified by crystallization from a 1/1 hexane/ethyl acetate mixture. 2 g of 2-[(1-benzoyl-1H-indazol-3-yl)methoxy]-2-methylpropanoic acid were obtained, m.p.=132-135° C.

$^1$H-NMR (CDCl$_3$, δ ppm): 1.61 (s, 6H), 4.93 (s, 2H), 7.41 (t, J=7.60 Hz, 1H), 7.46-7.66 (m, 4H), 8.02-8.09 (m, 3H), 8.68 (bs, 1H), 8.53 (d, J=8.42 Hz, 1H).

Preparation of Compound 4

2-{[1-(4-chlorobenzyl)-1H-indazol-3-yl]methoxy}-2-methylpropanoic acid

4a) [1-(4-chlorobenzyl)-1H-indazol-3-yl]methanol

The product was obtained using the method described in Example 1a), using 4-chlorobenzyl chloride as reagent.

The product obtained was purified by crystallization from a 5/1 hexane/ethyl acetate mixture.

m.p.=102-104° C.

$^1$H-NMR (CDCl$_3$, δ ppm): 3.5 (bs, 1H), 5.01 (s, 2H), 5.37 (s, 2H), 6.8-7.5 (m, 7H), 7.81 (d, J=7.82 Hz, 1H).

4b) 2-{[1-(4-chlorobenzyl)-1H-indazol-3-yl]methoxy}-2-methylpropanoic acid

The product was obtained using the method described in Example 1b, using [1-(4-chlorobenzyl)-1H-indazol-3-yl]methanol as reagent.

The product obtained was purified by crystallization from toluene.

m.p.=186-188° C.

$^1$H-NMR (CDCl$_3$, δ ppm): 1.61 (s, 6H), 4.91 (s, 2H), 5.54 (s, 2H), 7.0-7.5 (m, 7H), 8.07 (s, 1H), 10.3 (bs, 1H).

Preparation of Compound 5

2-[(1-benzyl-5-chloro-1H-indazol-3-yl)methoxy]-2-methylpropanoic acid

To a suspension of 2-[(1-benzyl-1H-indazol-3-yl)methoxy]-2-methylpropanoic acid (20 g; 0.062 mol), prepared as described in patent EP 0 382 276, in glacial acetic acid (250 ml), stirred at a temperature of about 20° C. in a heating bath, was added Cl$_2$ by bubbling until the starting material was consumed, as evidenced by TLC. The solution was then poured into water and ice (1 L) and stirred at room temperature overnight. The solid thus formed was filtered off and then crystallized once from 95° ethanol and a second time from a 1/1 hexane/ethyl acetate mixture.

5.5 g of 2-[(1-benzyl-5-chloro-1H-indazol-3-yl)methoxy]-2-methylpropanoic acid were obtained.

m.p.=145-147° C.

$^1$H-NMR (CDCl$_3$, δ ppm): 1.61 (s, 6H), 4.91 (s, 2H), 5.55 (s, 2H), 7.13-7.34 (m, 7H), 7.88 (d, J=1.83 Hz, 1H), 8.67 (bs, 1H).

Preparation of Compound 6

2-[(1-benzyl-5-nitro-1H-indazol-3-yl)methoxy]-2-methylpropanoic acid

6a) 2-methyl-2-[(5-nitro-1H-indazol-3-yl)methoxy]propanoic acid

To a mixture of 65% HNO$_3$ (100 ml) and concentrated H$_2$SO$_4$ (100 ml) stirred at about 10-20° C. was added 2-(1H-indazol-3-ylmethoxy)-2-methylpropanoic acid (25 g; 0.107 mol). The mixture was stirred at a controlled temperature of less than or equal to 20° C. until dissolution of the starting material was complete. The solution was then poured into water and ice (about 1 L) and the solid thus formed was filtered off and washed on the filter first with water and then with methanol.

26 g of 2-methyl-2-[(5-nitro-1H-indazol-3-yl)methoxy]propanoic acid were obtained, and were used for the following reaction without further purification.

m.p.=210° C. with decomposition $^1$H-NMR (CDCl$_3$+DMSO-d6, δ ppm): 1.58 (s, 6H), 4.91 (s, 2H), 7.54 (d, J=9.18 Hz, 1H), 8.19 (dd, J1, J2=9.18; 2.15 Hz, 1H), 9.13 (d, J=2.15 Hz, 1H), 12.5 (bs, 1H).

6b) 2-[(5-nitro-1-benzyl-1H-indazol-3-yl)methoxy]-2-methylpropanoic acid

To a solution of 2-methyl-2-[(5-nitro-1H-indazol-3-yl)methoxy]propanoic acid (26 g; 0.093 mol) in DMF (200 ml) was added 60% NaH (10 g; 0.25 mol) and the mixture was stirred for 10 minutes at 60° C. Benzyl chloride (25 ml; 0.217 mol) was then added to the mixture and the whole was stirred at 60° C. for 18 hours. The reaction was stopped by pouring the mixture into water (1 L), followed by acidifying with 5 N HCl and extracting the product with diethyl ether (3×250 ml). The residue obtained was dissolved in 95° ethanol (100 ml) and treated at reflux with 1N NaOH (200 ml) for 2 hours. The solution was then cooled to room temperature and washed with diethyl ether (3×200 ml). The alkaline phase was then acidified with concentrated HCl and extracted with ethyl acetate (3×300 ml). The combined organic phases were concentrated under reduced pressure and the crude residue obtained was purified by crystallization from ethyl acetate.

16 g of 2-[(5-nitro-1-benzyl-1H-indazol-3-yl)methoxy]-2-methylpropanoic acid were thus obtained.

m.p.=129-131° C.

$^1$H-NMR (CDCl$_3$, δ ppm): 1.64 (s, 6H), 4.99 (s, 2H), 5.59 (s, 2H), 7.80 (bs, 1H), 7.15-7.39 (m, 6H), 8.20 (dd, J=9.24; 2.10 Hz, 1H), 9.00 (d, J=2.20 Hz, 1H).

Preparation of Compound 7

2-{[1-(3,4-dichlorobenzyl)-1H-indazol-3-yl]methoxy}-2-methylpropanoic acid

7a) [1-(3,4-dichlorobenzyl)-1H-indazol-3-yl]methanol

The product was obtained via the method described in Example 1a), using 3,4-chlorobenzyl chloride as reagent.

The product obtained was purified by crystallization from a 1/1 hexane/ethyl acetate mixture.

m.p.=118-120° C.

$^1$H-NMR (CDCl$_3$, δ ppm): 3.1-3.3 (m, 1H), 4.9-5.2 (m, 2H), 5.38 (s, 2H), 6.89 (dd, J1, J2=8.27; 2.05 Hz, 1H), 7.1-7.5 (m, 5H), 7.82 (dt, J1, J2=8.01; 0.93, 1H).

7b) 2-{[1-(3,4-dichlorobenzyl)-1H-indazol-3-yl]methoxy}-2-methylpropanoic acid

The product was obtained via the method described in Example 1b), using [1-(3,4-dichlorobenzyl)-1H-indazol-3-yl]methanol as starting reagent.

The product obtained was purified by crystallization from toluene.

m.p.=174-176° C.

$^1$H-NMR (DMSO-d6, δ ppm): 1.44 (s, 6H), 4.76 (s, 2H), 5.64 (s, 2H), 7.12-7.22 (m, 2H), 7.41 (t, J=7.68 Hz, 1H), 7.54 (d, J=2.01 Hz, 1H), 7.58 (d, J=8.42 Hz, 1H), 7.72 (d, J=8.42 Hz, 1H), 7.95 (d, J=8.05 Hz, 1H), 12.81 (bs, 1H).

Preparation of Compound 8

2-methyl-2-{[1-(1,2,3,4-tetrahydronaphth-1-yl)-1H-indazol-3-yl]methoxy}-propanoic acid The product was prepared according to the procedure described in Example 6b), using as starting material 2-methyl-2-[(1-benzyl-1H-indazol-3-yl)methoxy]propanoic acid as starting material and 1-chloro-1,2,3,4-tetrahydronaphthalene as reagent.

The product was purified by crystallization from a 1/1 hexane/ethyl acetate mixture.

m.p.=132-134° C.

$^1$H-NMR (CDCl$_3$, δ ppm): 1.60 (d, J=2.15 Hz, 6H), 1.84-2.02 (m, 1H), 2.03-2.18 (m, 1H), 2.23-2.46 (m, 2H), 2.90 (dt, J=16.50; 4.85 Hz, 1H), 2.98-3.12 (m, 1H), 4.95 (s, 2H), 5.92 (dd, J=8.83; 6.52 Hz, 1H), 6.71 (d, J=7.76 Hz, 1H), 6.93-7.05 (m, 2H), 7.08-7.32 (m, 4H), 7.85 (d, J=8.09 Hz, 1H).

Preparation of Compound 17

{[1-(4-fluorobenzyl)-1H-indazol-3-yl]methoxy}acetic acid

17a) [1-(4-fluorobenzyl)-1H-indazol-3-yl]methanol

The product was prepared via the procedure described in Example 1a), using 4-fluorobenzyl chloride as reagent.

The product was purified by crystallization from hexane.

m.p.=80-81° C.

$^1$H-NMR CDCl$_3$, δ ppm): 3.4 (bs, 1H), 5.02 (s, 2H), 5.38 (s, 2H), 6.7-7.5 (m, 7H), 7.83 (d, J=8.01 Hz, 1H).

17b) {[1-(4-fluorobenzyl)-1H-indazol-3-yl]methoxy}acetic acid

A suspension containing [1-(4-fluorobenzyl)-1H-indazol-3-yl]methanol (6 g; 0.022 mol), bromoacetic acid (4 g; 0.03 mol) and 50% NaH (3 g; 0.066 mol) in THF (170 ml) was stirred at reflux for 72 hours. The reaction was then stopped by diluting with a suspension with water and ice (300 ml) and washing the aqueous phase with diethyl ether (3×150 ml). The aqueous phase was acidified with concentrated HCl. The solid thus formed was filtered off and purified by crystallization from isopropanol. 4 g of {[1-(4-fluorobenzyl)-1H-indazol-3-yl]methoxy}acetic acid were thus obtained.

m.p.=135-136° C.

$^1$H-NMR (DMSO-d6, δ ppm): 4.10 (s, 2H), 4.87 (s, 2H), 5.63 (s, 2H), 7.08-7.21 (m, 3H), 7.24-7.33 (m, 2H), 7.40 (t, J=7.68 Hz, 1H), 7.70 (d, J=8.42 Hz, 1H), 7.88 (d, J=8.05 Hz, 1H), 12.68 (bs, 1H).

Preparation of Compound 18

{[1-(2,4-dichlorobenzyl)-1H-indazol-3-yl]methoxy}acetic acid

18a) [1-(2,4-dichlorobenzyl)-1H-indazol-3-yl]methanol

The product was prepared via the procedure described in Example 1a), using 2,4-dichlorobenzyl chloride as reagent.

The product was purified by crystallization from a 7/3 ethanol/water mixture.

m.p.=105-106° C.

$^1$H-NMR (CDCl$_3$, δ ppm): 3.0 (bs, 1H), 5.04 (s, 2H), 5.52 (s, 2H), 6.58 (d, J=8.36 Hz, 1H), 6.96 (dd, J=8.34; 2.07 Hz, 1H), 7.1-7.5 (m, 4H), 7.84 (dt, J=9.79; 1.12 Hz, 1H).

18b) {[1-(2,4-dichlorobenzyl)-1H-indazol-3-yl]methoxy}acetic acid

The product was obtained via the method described in Example 17b, using as starting material [1-(2,4-dichlorobenzyl)-1H-indazol-3-yl]methanol.

The product was purified by crystallization from isopropanol.

m.p.=144-145° C.

$^1$H-NMR (DMSO-d6, δ ppm): 4.10 (s, 2H), 4.86 (s, 2H), 5.70 (s, 2H), 6.86 (d, J=8.42 Hz, 1H), 7.19 (ddd, J=8.05; 7.04; 0.82 Hz, 1H), 7.35 (dd, J=8.42; 2.20 Hz, 1H), 7.42 (ddd, J=8.32; 7.04; 1.10 Hz, 1H), 7.63-7.69 (m, 2H), 7.91 (dt, J=8.05; 0.91 Hz, 1H), 12.68 (bs, 1H).

Preparation of Compound 19

{2-[(1-benzyl-1H-indazol-3-yl)methoxy]ethoxy}acetic acid 19a) 2-[(1-benzyl-1H-indazol-3-yl)methoxy]ethanol To a solution of NaOH (2.8 g; 0.07 mol) in ethylene glycol (150 ml) stirred at room temperature was added 1-benzyl-3-chloromethylindazole, prepared as described in EP 0 382 276 (17.6 g; 0.07 mol). The solution was heated at 130° C. for 4 hours and then cooled to room temperature and the solvent was evaporated off under reduced pressure. The residue was taken up in water (100 ml) and the product was extracted with ethyl acetate (3×100 ml). The combined organic phases were concentrated under reduced pressure and the crude residue obtained was purified by crystallization from an approximately 1/1 hexane/ethyl acetate mixture.

13.8 g of 2-[(1-benzyl-1H-indazol-3-yl)methoxy]ethanol were thus obtained.

m.p.=67-69° C.

$^1$H-NMR (CDCl$_3$, δ ppm): 2.15 (bs, 1H), 3.61-3.82 (m, 4H), 4.97 (s, 2H), 5.57 (s, 2H), 7.11-7.38 (m, 8H), 7.81 (dt, J=8.15; 0.97 Hz, 1H).

19b) {2-[(1-benzyl-1H-indazol-3-yl)methoxy]ethoxy}acetic acid

To a solution of 2-[(1-benzyl-1H-indazol-3-yl)methoxy]ethanol (11.28 g, 0.04 mol) in dry tetrahydrofuran (THF) (100 ml) stirred at room temperature was added 60% sodium hydride (1.6 g, 0.04 mol). The mixture was heated at the boiling point for 2 hours and then cooled to room temperature, and a solution of ethyl bromoacetate (7.4 g, 0.044 mol) in THF (7 ml) was slowly added thereto. Once the addition was complete, the mixture was refluxed for a further 2 hours. The reaction was stopped by cooling to room temperature and evaporating off the solvent under reduced pressure. The residue was taken up in 2N NaOH (100 ml) and the product was extracted with diethyl ether (3×150 ml). The combined organic phases were concentrated under reduced pressure.

The crude residue was taken up in a solution of NaOH (1.9 g, 0.045 mol) in a 1/1 water/ethanol mixture (160 ml). The mixture was then stirred at reflux for 2 hours. The reaction was stopped by concentrating the solvent under reduced pressure, and the residue was taken up in water (100 ml) and washed with diethyl ether (3×50 ml). The alkaline phase was then acidified with concentrated HCl and the solid formed was filtered off. The product was purified by double crystallization from a 1/3 hexane/ethyl acetate mixture.

5.8 g of {2-[(1-benzyl-1H-indazol-3-yl)methoxy]ethoxy}acetic acid were obtained.

m.p.=101-103° C.

$^1$H-NMR (CDCl$_3$, δ ppm): 3.66-3.79 (m, 4H), 4.13 (s, 2H), 5.01 (s, 2H), 5.58 (s, 2H), 7.66 (bs, 1H), 7.14-7.40 (m, 8H), 7.84 (dt, J=8.11; 0.99 Hz, 1H).

Preparation of Compound 20

2-{2-[(1-benzyl-1H-indazol-3-yl)methoxy]ethoxy}-2-methylpropanoic acid

To a mixture of 2-[(1-benzyl-1H-indazol-3-yl)methoxy]ethanol (35 g, 0.124 mol) and NaOH (63 g, 1.57 mol) in acetone (180 ml) and water (1 ml), stirred at room temperature, was slowly added a 1/1 chloroform/acetone mixture (80 ml). During the addition, the temperature rose to the reflux point. Once the addition was complete, the solvent was evaporated off under reduced pressure and the residue was taken up in water (100 ml) and washed with diethyl ether (3×50 ml). The aqueous phase was acidified with glacial acetic acid and then extracted with diethyl ether (3×150 ml). The combined organic phases were concentrated under reduced pressure. The crude residue obtained was purified by crystallization from a 1/1 hexane/ethyl acetate mixture.

12.4 g of 2-{2-[(1-benzyl-1H-indazol-3-yl)methoxy]ethoxy}-2-methylpropanoic acid were obtained.

m.p.=94-95° C.

$^1$H-NMR (CDCl$_3$, δ ppm): 1.43 (s, 6H), 3.56-3.63 (m, 2H), 3.65-3.71 (m, 2H), 5.03 (s, 2H), 5.58 (s, 2H), 7.13-7.39 (m, 8H), 7.83 (dt, J=8.05; 0.82 Hz, 1H), 9.60 (bs, 1H).

Preparation of Compound 21

2-{3-[(1-benzyl-1H-indazol-3-yl)methoxy]propoxy}-2-methylpropanoic acid 21a) 3-[(1-benzyl-1H-indazol-3-yl)methoxy]propan-1-ol To a solution of NaOH (2.8 g; 0.07 mol) in 1,3-propanediol (150 ml) stirred at room temperature was added 1-benzyl-3-chloromethylindazole, prepared as described in EP 0 382 276 (17.6 g; 0.07 mol). The solution was heated at 130° C. for 4 hours and then cooled to room temperature, and the solvent was evaporated off under reduced pressure. The residue was taken up in water (100 ml) and the product was extracted with ethyl acetate (3×100 ml). The combined organic phases were concentrated under reduced pressure and the crude residue obtained was purified by flash chromatography on silica gel, using an approximately 1/1 hexane/ethyl acetate mixture as eluent.

10.5 g of 3-[(1-benzyl-1H-indazol-3-yl)methoxy]propan-1-ol were thus obtained.

$^1$H-NMR (CDCl$_3$, δ ppm): 1.85 (q, J=5.83 Hz, 2H), 2.75 (bs, 1H), 3.71 (t, J=7.74 Hz, 4H), 4.91 (s, 2H), 5.55 (s, 2H), 7.0-7.4 (m, 8H), 7.80 (d, J=7.77 Hz, 1H).

21 b) 2-{3-[(1-benzyl-1H-indazol-3-yl)methoxy]propoxy}-2-methylpropanoic acid

The product was obtained via the method described in Example 20, using as starting material 3-[(1-benzyl-1H-indazol-3-yl)methoxy]propan-1-ol. The product was purified by double crystallization from a 7/3 hexane/ethyl acetate mixture.

m.p.=57-59° C.

$^1$H-NMR (DMSO-d6, δ ppm): 1.25 (s, 6H), 1.72 (quint., J=6.40 Hz, 2H), 3.37 (t, J=6.40 Hz, 2H), 3.53 (t, J=6.40 Hz, 2H), 4.77 (s, 2H), 5.62 (s, 2H), 7.14 (ddd, J=8.00; 7.00; 0.73 Hz, 1H), 7.19-7.33 (m, 5H), 7.38 (ddd, J=8.37; 7.00; 0.91 Hz, 1H), 7.66 (d, J=8.42 Hz, 1H), 7.79 (dt, J=8.05; 0.91 Hz, 1H), 12.46 (s, 1H).

Preparation of Compound 22

2-{[1-(4-methylbenzyl)-1H-indazol-3-yl]methoxy}-2-methylpropanoic acid

22a) [1-(4-methylbenzyl)-1H-indazol-3-yl]methanol

The product was obtained via the method described in Example 1a, using 4-methylbenzyl chloride as reagent.

The product obtained was purified by crystallization from a 5/1 hexane/ethyl acetate mixture.

m.p.=90-92° C.

$^1$H-NMR (CDCl$_3$, δ ppm): 2.24 (s, 3H), 3.4 (bs, 1H), 5.0 (s, 2H), 5.36 (s, 2H), 6.9-7.4 (m, 7H), 7.79 (d, J=7.84 Hz, 1H).

22b) 2-{[1-(4-methylbenzyl)-1H-indazol-3-yl]methoxy}-2-methylpropanoic acid

The product was obtained via the method described in Example 1b), using [1-(4-methylbenzyl)-1H-indazol-3-yl]methanol as reagent.

The product obtained was purified by crystallization from toluene.

m.p.=160-162° C.

$^1$H-NMR (DMSO-d6, δ ppm): 1.45 (s, 6H), 2.23 (s, 3H), 4.75 (s, 2H), 5.55 (s, 2H), 6.9-7.2 (m, 5H), 7.37 (t, J=6.98 Hz, 1H), 7.64 (d, J=8.32 Hz, 1H), 7.94 (d, J=8.32 Hz, 1H).

Preparation of Compound 23

2-[(1-benzyl-5-bromo-1H-indazol-3-yl)methoxy]-2-methylpropanoic acid

To a suspension of 2-[(1-benzyl-1H-indazol-3-yl)methoxy]-2-methylpropanoic acid (17.5 g; 0.054 mol) in glacial acetic acid (75 ml), stirred at about 10° C. by means of a heating bath, was added dropwise a solution of Br$_2$ (10 ml; 0.195 mol) in glacial acetic acid (75 ml). Once the addition was complete, the solution was stirred at room temperature for 30 minutes and then poured into water (300 ml). Saturated Na$_2$SO$_3$ solution (100 ml) was then added to the mixture and the product was extracted with ethyl acetate (3×200 ml). The combined organic phases were concentrated under reduced pressure and the crude residue obtained was purified by crystallization from a 1/1 hexane/ethyl acetate mixture.

8 g of 2-[(1-benzyl-5-bromo-1H-indazol-3-yl)methoxy]-2-methylpropanoic acid were obtained.

m.p.=168-170° C.

$^1$H-NMR (CDCl$_3$, δ ppm): 1.61 (s, 6H), 4.91 (s, 2H), 5.54 (s, 2H), 8.11 (bs, 1H), 7.11-7.33 (m, 6H), 7.40 (dd, J=8.87; 1.74 Hz, 1H), 8.04 (d, J=1.83 Hz, 1H).

Preparation of Compound 24

2-[(5-amino-1-benzyl-1H-indazol-3-yl)methoxy]-2-methylpropanoic acid

To a suspension of 2-methyl-2-[(5-nitro-1-benzyl-1H-indazol-3-yl)-methoxy]propanoic acid (compound 6) (5.6 g; 0.015 mol) in methanol (50 ml) stirred at room temperature was added ammonium formate (5.5 g; 0.087 mol), followed by very slow addition of 10% palladium-on-charcoal (1 g; 0.9 mmol). Once the additions were complete, the mixture was stirred at room temperature for 30 minutes and then filtered, and the solution was concentrated under reduced pressure. The residue was taken up in water (100 ml) and the mixture was neutralized with glacial acetic acid. The solid thus formed was filtered off and purified by crystallization from a 1/1 ethyl acetate/ethanol mixture.

3 g of 2-methyl-2-[(5-amino-1-benzyl-1H-indazol-3-yl)methoxy]propanoic acid were thus obtained.

m.p.=172-173° C.

$^1$H-NMR (DMSO-d6+D$_2$O, δ ppm): 1.43 (s, 6H), 4.64 (s, 2H), 5.47 (s, 2H), 6.0-8.0 (bm, 11H).

Preparation of Compound 25

{[1-(4-chloro-2-methylbenzyl)-1H-indazol-3-yl]methoxy}acetic acid

The product was obtained via the method described in Example 17b, using as starting material [1-(4-chloro-2-methylbenzyl)-1H-indazol-3-yl]methanol.

The product was purified by crystallization from isopropanol.

m.p.=144-146° C.

$^1$H-NMR (DMSO-d6, δ ppm): 2.34 (s, 3H), 4.12 (s, 2H), 4.88 (s, 2H), 5.63 (s, 2H), 6.71 (d, J=8.19 Hz, 1H), 7.0-7.5 (m, 4H), 7.62 (d, J=8.19 Hz, 1H), 7.91 (d, J=7.69 Hz, 1H).

Preparation of Compound 29

2-[(1-benzyl-1H-indazol-3-yl)methoxy]-2-methylpropanoic acid

The preparation of product 29 was performed as described in patent application EP 382 276.

Preparation of Compound 33

{3-[(1-benzyl-1H-indazol-3-yl)methoxy]propoxy}acetic acid 33a) 3-[(1-benzyl-1H-indazol-3-yl)methoxy]propan-1-ol To a solution of NaOH (2.8 g; 0.07 mol) in 1,3-propanediol (150 ml) stirred at room temperature was added 1-benzyl-3-chloromethylindazole, prepared as described in Example 2a of EP 382 276 (17.6 g; 0.07 mol). The solution was heated at 130° C. for 4 hours and then cooled to room temperature, and the solvent was evaporated off under reduced pressure. The residue was taken up in water (100 ml) and the product was extracted with ethyl acetate (3×100 ml). The combined organic phases were concentrated under reduced pressure and the crude residue obtained was purified by flash chromatography on silica gel, using as eluent a 1/1 hexane/ethyl acetate mixture. The product was purified by crystallization from an approximately 1/1 hexane/ethyl acetate mixture.

$^1$H-NMR (CDCl$_3$, δ ppm): 1.85 (q, J=5.83 Hz, 2H), 2.75 (bs, 1H), 3.71 (t, J=7.74 Hz, 4H), 4.91 (s, 2H), 5.55 (s, 2H), 7.0-7.4 (m, 8H), 7.80 (d, J=7.77 Hz, 1H).

33b) {3-[(1-benzyl-1H-indazol-3-yl)methoxy]propoxy}acetic acid

To a solution of 3-[(1-benzyl-1H-indazol-3-yl)methoxy]propan-1-ol (11.5 g, 0.04 mol) in dry tetrahydrofuran (THF) (100 ml) stirred at room temperature was added 60% sodium hydride (1.6 g, 0.04 mol). The mixture was heated at the boiling point for 2 hours and then cooled to room temperature, and a solution of ethyl bromoacetate (7.4 g, 0.044 mol) in THF (7 ml) was slowly added thereto. Once the addition was complete, the mixture was refluxed for a further 2 hours. The reaction was stopped by cooling to room temperature and evaporating off the solvent under reduced pressure. The residue was taken up in 2N NaOH (100 ml) and the product was extracted with diethyl ether (3×150 ml). The combined organic phases were concentrated under reduced pressure.

The crude residue was taken up in a solution of NaOH (1.9 g, 0.045 mol) in a 1/1 water/ethanol mixture (160 ml). The mixture was then stirred at reflux for 2 hours. The reaction was stopped by concentrating the solvent under reduced pressure, and the residue was taken up in water (100 ml) and washed with diethyl ether (3×50 ml). The alkaline phase was then acidified with concentrated HCl and the solid formed was filtered off. The product was purified by double crystallization from a 1/3 hexane/ethyl acetate mixture. 5.5 g of {3-[(1-benzyl-1H-indazol-3-yl)methoxy]propoxy}acetic acid were thus obtained.

Preparation of Compound 34

{2-[(1-benzyl-1H-indazol-3-yl)methoxy]-2-methylpropoxy}acetic acid 34a) 2-[(1-benzyl-1H-indazol-3-yl)methoxy]-2-methylpropan-1-ol To a suspension of LiAlH4 (4.48 g; 0.118 mol) in diethyl ether (100 ml) stirred at room temperature was slowly added a solution of methyl 2-[(1-benzyl-1H-indazol-3-yl)methoxy]-2-methylpropanoate, prepared according to the method described in EP 0 382 276, (20 g; 0.06 mol) in diethyl ether (200 ml) and THF (50 ml). Once the addition was complete, the mixture was stirred at room temperature for 30 minutes and the reaction was then completed by adding 10 N NaOH (20 ml) and water (40 ml). The solvent was evaporated off under reduced pressure and the oily residue was purified by distillation at 0.01 mmHg at 190° C. The solid product thus obtained was crystallized from isopropanol.

11 g of 2-[(1-benzyl-1H-indazol-3-yl)methoxy]-2-methylpropan-1-ol were thus obtained.

m.p.=52-53° C.

¹H-NMR (CDCl₃, δ ppm): 1.34 (s, 6H), 2.50 (bs, 1H), 3.51 (s, 2H), 4.87 (s, 2H), 5.55 (s, 2H), 7.14 (ddd, J=8.04; 6.21; 1.68 Hz, 1H), 7.17-7.38 (m, 7H), 7.78 (dt, J=8.08; 1.00 Hz, 1H).

34b) {2-[(1-benzyl-1H-indazol-3-yl)methoxy]-2-methylpropoxy}acetic acid

To a solution of 2-[(1-benzyl-1H-indazol-3-yl)methoxy]-2-methylpropan-1-ol (11.0 g, 0.04 mol) in dry tetrahydrofuran (THF) (100 ml) stirred at room temperature was added 60% sodium hydride (1.6 g, 0.04 mol). The mixture was heated at the boiling point for 2 hours and then cooled to room temperature, and a solution of ethyl bromoacetate (7.4 g, 0.044 mol) in THF (7 ml) was slowly added thereto. Once the addition was complete, the mixture was refluxed for further 2 hours. The reaction was stopped by cooling to room temperature and evaporating off the solvent under reduced pressure. The residue was taken up in 2N NaOH (100 ml) and the product was extracted with diethyl ether (3×150 ml). The combined organic phases were concentrated under reduced pressure.

The crude residue was taken up in a solution of NaOH (1.9 g, 0.045 mol) in a 1/1 water/ethanol mixture (160 ml). The mixture was then stirred at reflux for 2 hours. The reaction was stopped by concentrating the solvent under reduced pressure, and the residue was taken up in water (100 ml) and washed with diethyl ether (3×50 ml). The alkaline phase was then acidified with concentrated HCl and the solid formed was filtered off. The product was purified by double crystallization from a 1/2 hexane/ethyl acetate mixture. 4.6 g of {2-[(1-benzyl-1H-indazol-3-yl)methoxy]-2-methylpropoxy}acetic acid were thus obtained.

Example 1

Analysis of the Gene Expression of MCP-1 in a Human Monocyte Line

The capacity of the compounds to inhibit the expression of MCP-1 by lipopolysaccharide (LPS)-stimulated MonoMac6 cells was evaluated. The cells were placed in 96-well plates at a concentration of 50 000 cells/well. The compounds were tested at the maximum soluble concentration given in Table 1 (in the range 30-300 μM) and incubated for 1 hour. The cells were then stimulated with LPS (100 ng/ml) for 4 hours.

The total RNA was extracted from the cell pellet using the RNeasy mini kit (Qiagen), reverse-transcribed with the TaqMan Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human MCP-1 was used (Applied Biosystems, RefSeq NM_002982.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 1 below.

TABLE 1

| No. | % inhibition | [μM] |
|---|---|---|
| 1 | 57 | 300 |
| 3 | 65 | 300 |
| 4 | 26 | 150 |
| 6 | 95 | 150 |
| 17 | 26 | 300 |
| 20 | 29 | 300 |
| 21 | 61 | 300 |

As shown by the results obtained and given in Table 1, the compounds were capable of significantly inhibiting the LPS-induced expression of MCP-1 in a human monocyte line, and showed a reduction in the levels of specific mRNA between 26% and 95%.

Example 2

Measurement of the Production of MCP-1 in a Human Monocyte Line

The capacity of the compounds to inhibit the expression of the protein MCP-1 by lipopolysaccharide (LPS)-stimulated MonoMac6 cells was evaluated. The cells were placed in 96-well plates at a concentration of 50 000 cells/well. The compounds were tested at the maximum soluble concentration given in Table 2 (in the range 30-300 μM) and incubated for 1 hour. The cells were then stimulated with LPS (100 ng/ml) for 20 hours.

The amount of MCP-1 produced was measured in the supernatants, suitably diluted with buffer, by means of an immunoenzymatic test (ELISA) using a commercial kit (ELISA MCP-1/JE, R&D Systems).

The results obtained, expressed as a percentage of inhibition, are collated in Table 2 below.

TABLE 2

| No. | % inhibition | [μM] |
|---|---|---|
| 1 | 80 | 300 |
| 2 | 66 | 300 |
| 3 | 83 | 300 |
| 4 | 54 | 150 |
| 5 | 82 | 150 |
| 6 | 100 | 150 |
| 7 | 29 | 30 |
| 8 | 77 | 150 |
| 17 | 39 | 300 |
| 18 | 35 | 30 |
| 19 | 63 | 300 |
| 20 | 73 | 300 |
| 21 | 88 | 300 |
| 22 | 37 | 150 |

As shown by the results obtained and given in Table 2, the compounds were capable of significantly inhibiting the LPS-induced expression of MCP-1 in a human monocyte line, and showed a reduction in the levels of produced protein between 29% and 100%.

Example 3

Analysis of the Gene Expression of CX3CR1 in a Human Monocyte line

The capacity of the compounds to inhibit the expression of CX3CR1 by lipopolysaccharide (LPS)-stimulated MonoMac6 cells was evaluated. The cells were placed in 96-well plates at a concentration of 50 000 cells/well. The compounds were tested at the maximum soluble concentration given in Table 3 (in the range 30-300 μM) and incubated for 1 hour. The cells were then stimulated with LPS (100 ng/ml) for 20 hours.

The total RNA was extracted from the cell pellet using the RNeasy mini kit (Qiagen), reverse-transcribed with the Taq-Man Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human CX3CR1 was used (Applied Biosystems, RefSeq NM_001337.3). A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 3 below.

TABLE 3

| No. | % inhibition | [μM] |
|---|---|---|
| 1 | 97 | 300 |
| 3 | 99 | 300 |
| 4 | 87 | 150 |
| 6 | 98 | 150 |
| 7 | 85 | 30 |
| 17 | 90 | 300 |
| 20 | 89 | 300 |
| 21 | 97 | 300 |
| 29 | 75 | 300 |

As shown by the results obtained and given in Table 3, the compounds were capable of significantly inhibiting the LPS-induced expression of CX3CR1 in a human monocyte line, and showed a reduction in the levels of specific mRNA between 75% and 99%.

Example 4

Analysis of the Gene Expression of p40 in a Human Monocyte Line

The capacity of the compounds to inhibit the expression of p40 by lipopolysaccharide (LPS)-stimulated MonoMac6 cells was evaluated. The cells were placed in 96-well plates at a concentration of 50 000 cells/well. The compounds were tested at the maximum soluble concentration given in Table 4 (in the range 30-300 μM) and incubated for 1 hour. The cells were then stimulated with LPS (100 ng/ml) for 4 hours.

The total RNA was extracted from the cell pellet using the RNeasy mini kit (Qiagen), reverse-transcribed with the Taq-Man Reverse transcription reagents synthesis kit (Applied Biosystems) and the cDNA obtained was used for the real-time PCR reaction. The amplification was obtained in 96-well plates using the ABI Prism 7000 sequence detection system (Applied Biosystems), by applying the following temperature profile: 50° C. for 2 minutes, 95° C. for 10 minutes and 45 cycles at 95° C. for 15 seconds and 60° C. for 1 minute. For the amplification, a set of primers and probe specific for human p40 was used (Applied Biosystems, RefSeq NM_002187.2).

A set of primers and probe for β-actin was used in separate wells as an internal control of the samples for the purposes of normalization. Once the reaction had taken place, the fluorescence data were analysed using the ABI Prism 7000 SDS software, by calculating the threshold cycle (Ct) for each sample and subsequently performing a relative quantification via the ΔΔCt method.

The results obtained, expressed as a percentage of inhibition, are collated in Table 4 below.

TABLE 4

| No. | % inhibition | [μM] |
|---|---|---|
| 1 | 50 | 300 |
| 3 | 64 | 300 |
| 4 | 48 | 150 |
| 7 | 47 | 30 |
| 17 | 61 | 300 |
| 20 | 58 | 300 |
| 21 | 50 | 300 |
| 29 | 57 | 300 |

As shown by the results obtained and given in Table 4, the compounds were capable of significantly inhibiting the LPS-induced expression of p40 in a human monocyte line, and showed a reduction in the levels of specific mRNA between 47% and 64%.

The invention claimed is:
1. A compound of formula (I)

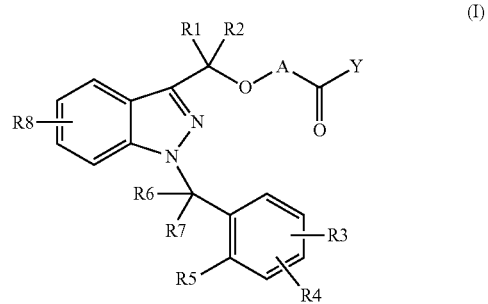

wherein:
A is —$X_1$— or —$X_1$—OC($R_9$)($R_{10}$)—, wherein
   $X_1$ is an alkyl group having from 1 to 5 carbon atoms, optionally substituted with one or more alkyl groups having from 1 to 5 carbon atoms or one or more alkoxy groups having from 1 to 3 carbon atoms, and
   $R_9$ and $R_{10}$, which are identical or different each other, are hydrogen, an alkyl group having from 1 to 5 carbon atoms or an alkoxy group having from 1 to 3 carbon atoms,
Y is OH
$R_1$ and $R_2$, which are identical or different each other, are hydrogen, an alkyl group having from 1 to 5 carbon atoms or an alkoxy group having from 1 to 3 carbon atoms,
$R_3$, $R_4$ and $R_8$, which are identical or different each other, are hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —SO$_2$NR'R", —SO$_2$R', or nitro and trifluoromethyl, wherein R' and R" are identical or different each other, and are represented by hydrogen and an alkyl group having from 1 to 5 carbon atoms, $R_5$ is hydrogen, an alkyl group having from 1 to 5 carbon atoms, an alkoxy group having from 1 to 3 carbon atoms, a halogen atom, —OH, —N(R')(R"), —N(R')COR", or nitro and trifluoromethyl, or $R_5$ together with one of $R_6$ and $R_7$ forms a ring having 5 or 6 carbon atoms, wherein R' and R" are identical or different each other, and are represented by hydrogen and an alkyl group having from 1 to 5 carbon atoms, $R_6$ and $R_7$, which are identical or different each other, are hydrogen, or an alkyl group having from 1 to 5 carbon atoms, or $R_6$ and $R_7$ together form a group C=O, or one of $R_6$ and $R_7$, together with $R_5$, forms a ring having 5 or 6 carbon atoms, wherein when A is an unsubstituted methylene group or a methylene group substituted with one or more alkyl groups having 1 to 5 carbon atoms, at least one of $R_3$ to $R_8$ is not a hydrogen, or a pharmaceutically acceptable salt thereof, an ester thereof or a prodrug thereof.

2. The compound according to claim 1, wherein $X_1$ is an alkyl group having from 1 to 3 carbon atoms, optionally substituted with one or more alkyl groups having from 1 to 3 carbon atoms or one or more alkoxy groups having 1 or 2 carbon atoms, or a pharmaceutically acceptable salt thereof, an ester thereof or a prodrug thereof.

3. The compound according to claim 1, wherein $X_1$ is selected from the group consisting of a group $CH_2$, a group $CH_2CH_2$, and a group $C(CH_3)_2$, and $R_9$ and $R_{10}$, which are identical or different each other, are hydrogen or a $CH_3$ group, or a pharmaceutically acceptable salt thereof, an ester thereof or a prodrug thereof.

4. The compound according to claim 1, wherein residue A is selected from the group consisting of a group $CH_2$, a group $CH_2CH_2$, a group $C(CH_3)_2$, a group $CH_2CH_2OCH_2$, a group $CH_2CH_2OC(CH_3)_2$ and a group $CH_2CH_2CH_2OC(CH_3)_2$, or a pharmaceutically acceptable salt thereof, an ester thereof or a prodrug thereof.

5. The compound according to claim 1, wherein $R_3$, $R_4$ and $R_8$, which are identical or different each other, are selected from the group consisting of a hydrogen atom, an alkyl group having from 1 to 3 carbon atoms, an alkoxy group having 1 or 2 carbon atoms, a Br, Cl or F atom, an OH group, a nitro group, a trifluoromethyl group, a group N(R')(R"), —N(R') COR", —CN, —CONR'R", —SO$_2$NR'R", and —SO$_2$R', wherein R' and R" are identical or different each other, and are represented by a hydrogen atom and an alkyl group having from 1 to 3 carbon atoms, or a pharmaceutically acceptable salt thereof, an ester thereof or a prodrug thereof.

6. The compound according to claim 1, wherein $R_5$ is selected from the group consisting of a hydrogen atom, an alkyl group having from 1 to 3 carbon atoms, an alkoxy group having 1 or 2 carbon atoms, a halogen atom, and an OH group, or $R_5$, together with one of $R_6$ and $R_7$, forms a ring having 5 or 6 carbon atoms, or a pharmaceutically acceptable salt thereof, an ester thereof or a prodrug thereof.

7. The compound according to claim 1, wherein $R_6$ and $R_7$, which are identical or different each other, are selected from the group consisting of a hydrogen atom, and an alkyl group having from 1 to 3 carbon atoms; or $R_6$ and $R_7$ together form a group C=O, or one of $R_6$ and $R_7$, together with $R_5$, forms a ring having 5 or 6 carbon atoms, or a pharmaceutically acceptable salt thereof, an ester thereof or a prodrug thereof.

8. A pharmaceutical composition comprising the compound of formula (I) according to claim 1, or a pharmaceutically acceptable salt, ester or prodrug thereof, and at least one pharmaceutically acceptable vehicle.

9. The pharmaceutical composition according to claim 8, wherein the pharmaceutically acceptable salt is an additional salt having a physiologically acceptable organic or mineral acid or base.

10. The pharmaceutical composition according to claim 9, wherein the physiologically acceptable acid is selected from the group consisting of hydrochloric acid, hydrobromic acid, sulfuric acid, phosphoric acid, nitric acid, acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

11. The pharmaceutical composition according to claim 9, wherein the physiologically acceptable base is selected from the group consisting of ammonium hydroxide, calcium hydroxide, magnesium carbonate, sodium hydrogen carbonate, potassium hydrogen carbonate, arginine, betaine, caffeine, choline, N,N-dibenzylethylene-diamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

12. The pharmaceutical composition according to claim 8, wherein the pharmaceutically acceptable ester is formed with a physiologically acceptable organic acid or alcohol.

13. The pharmaceutical composition according to claim 8, wherein the composition comprises a stereoisomer or an enantiomer of the compound of formula (I), or a pharmaceutically acceptable salt, ester or prodrug thereof, or a mixture thereof.

14. The pharmaceutical composition according to claim 8, wherein the pharmaceutically acceptable vehicle is selected from the group consisting of a glidant, a binder, a disintegrant, a filler, a diluent, a flavoring, a colorant, a fluidizer, a lubricant, a preserving agent, a humectant, an absorbent, and a sweetener.

15. A method for treating a disease having expression of MCP-1, CX3CR1 and p40, comprising administering an effective amount of a compound of formula (I), a pharmaceutically acceptable salt thereof, an ester thereof or a prodrug thereof to a living being in need thereof

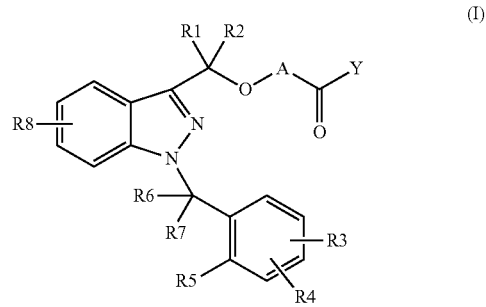

(I)

wherein:
A is —$X_1$— or —$X_1$—OC($R_9$)($R_{10}$)—, wherein
$X_1$ is an alkyl group having from 1 to 5 carbon atoms, optionally substituted with one or more alkyl groups having from 1 to 5 carbon atoms or one or more
alkoxy groups having from 1 to 3 carbon atoms, and
$R_9$ and $R_{10}$, which are identical or different each other,
are hydrogen, an alkyl group having from 1 to 5 carbon atoms or an alkoxy group having from 1 to 3 carbon atoms, Y is OH, $R_1$ and $R_2$, which are identical or different each other, are hydrogen, an alkyl group having from 1 to 5 carbon atoms or an alkoxy group having from 1 to 3 carbon atoms, $R_3$, $R_4$ and $R_8$, which are identical or different each other, are hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —SO$_2$NR'R", —SO$_2$R', or nitro and trifluoromethyl; wherein R' and R", are identical or different each other, and are represented by hydrogen and an alkyl group having from 1 to 5 carbon atoms, $R_5$ is hydrogen, an alkyl group having from 1 to 5 carbon atoms, an alkoxy group having from 1 to 3 carbon atoms, a halogen atom, —OH, —N(R')(R"), —N(R')COR", or nitro and trifluoromethyl, or $R_5$ together with one of $R_6$ and $R_7$ forms a ring having 5 or 6 carbon atoms, wherein R' and R" are identical or different each other, and are represented by hydrogen and an alkyl group having from 1 to 5 carbon atoms, $R_6$ and $R_7$, which are identical or different each other, are hydrogen, or an alkyl group having from 1 to 5 carbon atoms, or $R_6$ and $R_7$ together form a group C═O, or one of $R_6$ and $R_7$, together with $R_5$, forms a ring having 5 or 6 carbon atoms, wherein when A is an unsubstituted methylene group or a methylene group substituted with one or more alkyl groups having 1 to 5 carbon atoms, at least one of $R_3$ to $R_8$ is not a hydrogen.

16. The method according to claim 15, wherein the disease having the expression of MCP-1 and CX3CR1 is selected from the group consisting of articular diseases, renal diseases, cardiovascular diseases, metabolic syndrome, obesity, diabetes, insulin resistance and cancer.

17. The method according to claim 15, wherein the disease comprising the expression of MCP-1 is selected from the group consisting of rheumatoid arthritis, arthritis induced by a viral infection, psoriatic arthritis, arthrosis, lupus nephritis, diabetic nephropathy, glomerulonephritis, polycystic kidney disease, interstitial lung disease, fibrosis, multiple sclerosis, Alzheimer's disease, HIV-associated dementia, atopic dermatitis, psoriasis, vasculitis, restenosis, atherosclerosis, myocardial infarction, angina, acute coronary diseases, adenomas, carcinomas and metastases, metabolic diseases and a complication following a surgical intervention.

18. The method according to claim 15, wherein the disease comprising the expression of CX3CR1 is selected from the group consisting of rheumatoid arthritis, lupus nephritis, diabetic nephropathy, Crohn's disease, ulcerative colitis, coronary disorders, restenosis, atherosclerosis, myocardial infarction, angina, and a complication following a surgical intervention.

19. The method according to claim 15, wherein the disease having the expression of p40 is selected from the group consisting of an autoimmune disease, a chronic degenerative inflammatory disease, and cancer.

20. The method according to claim 15, wherein the disease comprising the expression of p40 is selected from the group consisting of rheumatoid arthritis, psoriasis, glomerulonephritis, diabetes, lupus erythematosus, diabetes, Crohn's disease, and a tumor.

21. A method for treating a disease having expression of CX3CR1 and p40, selected from the group consisting of lupus nephritis, diabetic nephropathy, Crohn's disease, ulcerative colitis, coronary disorders, restenosis, myocardial infarction, angina, a chronic degenerative inflammatory disease, psoriasis, type II diabetes, a tumor, and cancer, comprising administering an effective amount of a compound of formula (I), a pharmaceutically acceptable salt thereof, an ester thereof or a prodrug thereof to a person in need thereof:

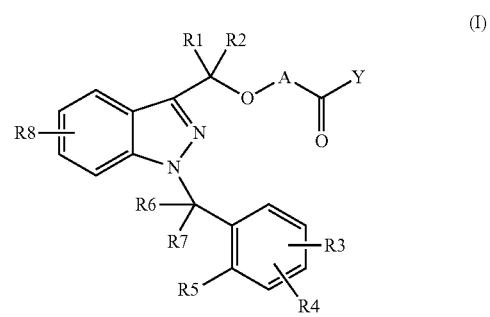

(I)

wherein:

A is —X$_1$— or —X$_1$—OC(R$_9$)(R$_{10}$)—, wherein
X$_1$ is an alkyl group having from 1 to 5 carbon atoms, optionally substituted with one or more alkyl groups having from 1 to 5 carbon atoms or one or more alkoxy groups having from 1 to 3 carbon atoms, and
$R_9$ and $R_{10}$, which are identical or different each other, are hydrogen, an alkyl group having from 1 to 5 carbon atoms or an alkoxy group having from 1 to 3 carbon atoms, Y is OH, $R_1$ and $R_2$, which are identical or different each other, are hydrogen, an alkyl group having from 1 to 5 carbon atoms or an alkoxy group having from 1 to 3 carbon atoms, $R_3$, $R_4$ and $R_8$, which are identical or different each other, are hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —SO$_2$NR'R", —SO$_2$R', or nitro and trifluoromethyl, wherein R' and R" are identical or different each other, and are represented by hydrogen and an alkyl group having from 1 to 5 carbon atoms, $R_5$ is hydrogen, an alkyl group having from 1 to 5 carbon atoms, an alkoxy group having from 1 to 3 carbon atoms, a halogen atom, —OH, —N(R')(R"), —N(R')COR", or nitro and trifluoromethyl, or $R_5$ together with one of $R_6$ and $R_7$ forms a ring having 5 or 6 carbon atoms, wherein R' and R" are identical or different each other, and are represented by hydrogen and an alkyl group having from 1 to 5 carbon atoms, and $R_6$ and $R_7$, which are identical or different each other, are hydrogen, or an alkyl group having from 1 to 5 carbon atoms, or $R_6$ and $R_7$ together form a group C═O, or one of $R_6$ and $R_7$, together with $R_5$, forms a ring having 5 or 6 carbon atoms.

22. A method for treating a disease having expression of MCP-1, CX3CR1 and p40, comprising administering an effective amount of a compound of formula (I), a pharmaceutically acceptable salt thereof, an ester thereof or a prodrug thereof to a person in need thereof:

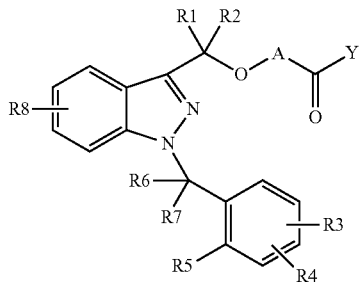

(I)

wherein:
A is —$X_1$— or —$X_1$—OC($R_9$)($R_{10}$)—, wherein
  $X_1$ is an alkyl group having from 1 to 5 carbon atoms, optionally substituted with one or more alkyl groups having from 1 to 5 carbon atoms or one or more alkoxy groups having from 1 to 3 carbon atoms, and
  $R_9$ and $R_{10}$, which are identical or different each other, are hydrogen, an alkyl group having from 1 to 5 carbon atoms or an alkoxy group having from 1 to 3 carbon atoms,
Y is OH
$R_1$ and $R_2$, which are identical or different each other, are hydrogen, an alkyl group having from 1 to 5 carbon atoms or an alkoxy group having from 1 to 3 carbon atoms,
$R_3$, $R_4$ and $R_8$, which are identical or different each other, are hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —$SO_2$NR'R", —$SO_2$R', or nitro and trifluoromethyl, wherein R' and R" are identical or different each other, and are represented by hydrogen and an alkyl group having from 1 to 5 carbon atoms,
$R_5$ is hydrogen, an alkyl group having from 1 to 5 carbon atoms, an alkoxy group having from 1 to 3 carbon atoms, a halogen atom, —OH, —N(R')(R"), —N(R')COR", or nitro and trifluoromethyl, or $R_5$ together with one of $R_6$ and $R_7$ forms a ring having 5 or 6 carbon atoms, wherein R' and R" are identical or different each other, and are represented by hydrogen and an alkyl group having from 1 to 5 carbon atoms, and
$R_6$ and $R_7$, which are identical or different each other, are hydrogen, or an alkyl group having from 1 to 5 carbon atoms, or $R_6$ and $R_7$ together form a group C=O, or one of $R_6$ and $R_7$, together with $R_5$, forms a ring having 5 or 6 carbon atoms,
wherein when Y is —OH, A is different from an alkyl group having 1 carbon atom, optionally substituted with one or more alkyl groups having from 1 to 5 carbon atoms, or alternatively at least one of $R_1$ to $R_8$ is different from hydrogen.

* * * * *